United States Patent
Amirkhanian et al.

(10) Patent No.: US 7,309,409 B2
(45) Date of Patent: *Dec. 18, 2007

(54) MULTI-CHANNEL BIO-SEPARATION CARTRIDGE

(75) Inventors: Varouj Amirkhanian, La Crescenta, CA (US); Ming-Sun Liu, Brea, CA (US); Paul Mooney, Rancho Santa Margarita, CA (US)

(73) Assignee: Biocal Technology, Inc., Irvine, CA (US)

( * ) Notice: Subject to any disclaimer, the term of this patent is extended or adjusted under 35 U.S.C. 154(b) by 385 days.

This patent is subject to a terminal disclaimer.

(21) Appl. No.: 10/059,993

(22) Filed: Jan. 28, 2002

(65) Prior Publication Data

US 2002/0123073 A1    Sep. 5, 2002

Related U.S. Application Data

(60) Provisional application No. 60/264,605, filed on Jan. 26, 2001.

(51) Int. Cl.
*G01N 27/26* (2006.01)
(52) U.S. Cl. ............... 204/603; 204/605; 204/616; 204/612
(58) Field of Classification Search ............... 435/7.1; 204/603, 612, 605, 606, 451, 456, 452, 461, 204/601, 602, 455
See application file for complete search history.

(56) References Cited

U.S. PATENT DOCUMENTS 4,417,967 A * 11/1983 Ledley .................. 204/466
4,827,780 A *  5/1989 Sarrine et al. ......... 73/864.21
5,062,942 A    11/1991 Kambara et al.
5,066,382 A * 11/1991 Weinberger et al. .... 204/451
5,192,412 A *  3/1993 Kambara et al. ....... 204/612

(Continued)

FOREIGN PATENT DOCUMENTS

EP    0021499    1/1981

(Continued)

OTHER PUBLICATIONS

Taylor et al, "Axial-Beam Laser-Excited Fluorescence Detection in Capillary Electrophoresis," Anal. Chem., (1992), vol. 64, pp. 1741-1744.*

(Continued)

*Primary Examiner*—Nam Nguyen
*Assistant Examiner*—Anthony Fick
(74) *Attorney, Agent, or Firm*—Liu & Liu

(57) ABSTRACT

A bio-separation system using an efficient, compact, portable, interchangeable, reusable, recyclable, multi-channel cartridge, has integrated pre-aligned optics and an integrated reagent reservoir. The cartridge supports, for example, multiple capillaries for CE separation. An integrated reservoir containing a separation support medium (e.g., a gel buffer) is common to all capillaries. The chemistry of the medium and the characteristics of the capillaries (e.g., capillary size, coating and length) are defined for each cartridge. Different cartridges can be easily interchanged in the bio-separation system to suit the particular sample based separation. The reservoir is coupled to an air pressure pump that pressurizes the gel reservoir to purge and fill the capillaries with buffer as the separation support medium. In another aspect of the present invention, optics requiring fine alignment with respect to the detection zones (such as fiber optics for directing incident radiation and/or radiation emissions) are integrated into the cartridge.

22 Claims, 17 Drawing Sheets

U.S. PATENT DOCUMENTS

| | | | |
|---|---|---|---|
| 5,198,091 A | 3/1993 | Burolla et al. | |
| 5,324,401 A | 6/1994 | Yeung et al. | |
| 5,338,427 A | 8/1994 | Shartle et al. | |
| 5,366,608 A | 11/1994 | Kambara | |
| 5,413,686 A | 5/1995 | Klein et al. | |
| 5,416,879 A | 5/1995 | Liu et al. | |
| 5,439,578 A | 8/1995 | Dovichi et al. | |
| 5,498,324 A | 3/1996 | Yeung et al. | |
| 5,529,679 A | 6/1996 | Takahashi et al. | |
| 5,543,018 A | 8/1996 | Stevens et al. | |
| 5,560,811 A * | 10/1996 | Briggs et al. | 204/451 |
| 5,584,982 A | 12/1996 | Dovichi et al. | |
| 5,625,403 A | 4/1997 | Hazman et al. | |
| 5,635,050 A * | 6/1997 | Pentoney et al. | 204/605 |
| 5,650,846 A | 7/1997 | Yin et al. | |
| 5,675,155 A | 10/1997 | Pentoney, Jr. et al. | |
| 5,741,411 A | 4/1998 | Yeung et al. | |
| 5,741,412 A | 4/1998 | Dovichi et al. | |
| 5,763,277 A | 6/1998 | Zhu et al. | |
| 5,790,727 A | 8/1998 | Dhadwal et al. | |
| 5,846,727 A | 12/1998 | Soper et al. | |
| 5,865,974 A * | 2/1999 | Cabilly et al. | 204/456 |
| 5,916,428 A | 6/1999 | Kane et al. | |
| 5,968,331 A | 10/1999 | Kambara et al. | |
| 6,001,230 A | 12/1999 | Burolla | |
| 6,013,165 A * | 1/2000 | Wiktorowicz et al. | 204/456 |
| 6,017,765 A | 1/2000 | Yamada et al. | |
| 6,027,627 A | 2/2000 | Li et al. | |
| 6,043,880 A | 3/2000 | Andrews et al. | |
| 6,054,032 A | 4/2000 | Haddad et al. | |
| 6,063,251 A | 5/2000 | Kane et al. | |
| 6,074,827 A | 6/2000 | Nelson et al. | |
| 6,084,667 A | 7/2000 | Melman et al. | |
| 6,103,083 A | 8/2000 | Merenkova et al. | |
| 6,104,485 A | 8/2000 | Wang et al. | |
| 6,132,578 A | 10/2000 | Kambara et al. | |
| 6,153,437 A | 11/2000 | Horn | |
| 6,184,990 B1 | 2/2001 | Amirkhanian et al. | |
| 6,326,213 B1 | 12/2001 | Letcher et al. | |
| RE37,606 E | 3/2002 | Guttman | |
| 6,369,893 B1 | 4/2002 | Christel et al. | |
| 6,375,819 B1 * | 4/2002 | Li et al. | 204/455 |
| 6,445,448 B1 * | 9/2002 | Melman et al. | 356/246 |
| RE37,941 E | 12/2002 | Guttman | |
| 6,752,914 B1 * | 6/2004 | Hassard | 204/603 |
| 6,828,567 B2 * | 12/2004 | Amirkhanian et al. | 250/458.1 |
| 6,870,165 B2 * | 3/2005 | Amirkhanian et al. | 250/458.1 |
| 2002/0092770 A1 | 7/2002 | Hedberg et al. | |
| 2002/0113213 A1 * | 8/2002 | Amirkhanian et al. | 250/458.1 |
| 2003/0052008 A1 * | 3/2003 | Liu et al. | 204/459 |
| 2003/0116436 A1 * | 6/2003 | Amirkhanian et al. | 204/452 |
| 2003/0178312 A1 * | 9/2003 | Amirkhanian et al. | 204/603 |

FOREIGN PATENT DOCUMENTS

| | | |
|---|---|---|
| EP | 0631134 A2 | 12/1994 |
| EP | 0723149 | 7/1996 |
| JP | 7174701 | 7/1995 |
| JP | 8136502 | 5/1996 |
| JP | 10-206384 A * | 8/1998 |
| JP | 11023533 | 1/1999 |
| JP | 11230938 | 8/1999 |
| JP | 2001-124736 A * | 5/2001 |
| WO | WO98/10122 | 3/1998 |
| WO | 9813667 | 4/1998 |
| WO | WO00/06996 | 2/2000 |
| WO | WO01/02846 | 1/2001 |
| WO | WO 02/28509 | 4/2002 |
| WO | WO 02/059589 | 8/2002 |

OTHER PUBLICATIONS

Taylor et al, "Multiplexed Fluorescence Detector for Capillary Electrophoresis Using Axial Optical Fiber Illumination," Anal. Chem., (1993), vol. 65, pp. 956-960.*

Ueno et al, "Simultaneous Monitoring of DNA Fragments Separated by Electrophoresis in a Multiplexed Array of 100 Capillaries," Anal. Chem., vol. 66, No. 9, pp. 1424-1431, May 1, 1994.*

The New Encyclopaedia Britannica, 15th Edition, vol. 25, (1994), p. 202.*

Quesada, M.A., Zhang, S., Multiple capillary DNA sequencer that uses fiber-optic illumination and detection, Electrophoresis, 17, 1996, pp. 1841-1851.*

International Search Report of Counterpart PCT Application No. PCT/US02/02514, Oct. 18, 2002.

International Search Report of Counterpart PCT Application No. PCT/US03/01841, Jul. 7, 2003.

"Low-Cost, High-Sensitivity Laser-Induced Fluorescence Detection for DNA Sequencing by Capillary Gel Electrophoresis", Chen, et al., Journal of Chromatography, vol. 559, 1991, pp. 237-246.

"Multiple Capillary DNA Sequencer that Uses Fiber-Optic Illumination and Detection", by Quesada, et al., Electrophoresis, vol. 17, 1996, pp. 1841-1851.

International Search Report of Counterpart PCT Application No. PCT/US02/02515, Feb. 11, 2003.

Partial International Search Report of Counterpart PCT Application No. PCT/US2004/043424.

Simultaneous Monitoring of DNA Fragments Separated by Electrophoresis in a Multiplexed Array of 100 Capillaries, year not available.

DNA Analysis Tools Shrink, year not available.

An Integrated Nanoliter DNA Analysis Device, year not available.

DNA Sequencing Using Capillary Array Electrophoresis, year not available.

Three DNA Sequencing Methods Using Capillary Gel Electrophoresis and Laser-Induced Fluorescence, year not available.

DNA Sequencing by Multiple Capillaries that Form a Waveguide, year not available.

A Capillary Array Gel Electrophoresis System Using Multiple Laser Focusing for DNA Sequencing, year not available.

Researchers Design DNA Lab on a Chip, year not available.

Laser-Induced Fluorescence Detection of a Single Molecule in a Capillary, year not available.

Up to Speed on PCR, year not available.

Low-Cost, High-Sensitivity Laser-Induced Fluorescence Detection for DNA Sequencing by Capillary Gel Electrophoresis, year not available.

Electrophoresis, 1996, 17, 1845-1851.

Taylor et al, Axial-Beam Laser-Excited Fluorescence Detection in Capillary Electrophoresis, Anal. Chem. 1992, vol. 64, 1741-1744.

Taylor et al, Multiplexed Fluorescence Detector for Capillary Electrophoresis Using Axial Optical Fiber Illumination, Anal. Chem. 1993, vol. 65, 956-960.

"Simultaneous Monitoring of DNA Fragments Separated by Electrophoresis in a Multiplexed Array of 100 Capillaries", by Ueno, et al., Analytical Chemistry, vol. 66, No. 9, May 1, 1994, pp. 1424-1431.

"DNA Analysis Tools Shrink", by Richard Gaughan, Biophotonics International, Jul./Aug. 2000, pp. 18-19.

"An Integrated Nanoliter DNA Analysis Device", by Burns, et al., Science, vol. 282, Oct. 16, 1998, pp. 484-487.

"DNA Sequencing Using Capillary Array Electrophoresis", by Huang, et al., Analytical Chemistry, vol. 64, No. 18, Sep. 15, 1992, pp. 2149-2154.

"Three DNA Sequencing Methods Using Capillary Gel Electrophoresis and Laser-Induced Fluorescence", by Swerdlow, et al., Analytical Chemistry, vol. 63, No. 24, Dec. 15, 1991, pp. 2835-2841.

"DNA Sequencing by Multiple Capillaries that Form a Waveguide", by Dhadwal, et al., pp. 1-14, year not available.

"A Capillary Array Gel Electrophoresis System Using Multiple Laser Focusing for DNA Sequencing", by Anazawa, et al., Analytical Chemistry, vol. 68, No. 15, Aug. 1, 1996, pp. 2699-2704.

"Researchers Design DNA Lab on a Chip", by Kate Leggett, Biophotonics International, Jan./Feb. 1999, p. 25.

"Laser-Induced Fluorescence Detection of a Single Molecule in a Capillary", by Lee, et al., Analytical Chemistry, vol. 66, No. 23, Dec. 1, 1994, pp. 4142-4149.

"Up to Speed on PCR", by Deborah A. Fitzgerald, The Scientist, Nov. 27, 2000, pp. 31-33.

"Low-Cost, High-Sensitivity Laser-Induced Fluorescence Detection for DNA Sequencing by Capillary Gel Electrophoresis", Chen, et al., Journal of Chromatography, vol. 559, 1991, pp. 237-246.

"Multiple Capillary DNA Sequencer that Uses Fiber-Optic Illumination and Detection", by Quesada, et al., Electrophoresis, vol. 17, 1996, pp. 1841-1851.

* cited by examiner

MULTI-CHANNEL BIO-SEPARATION CARTRIDGE

This application claims the priority of U.S. Provisional Patent Application No. 60/264,605, filed on Jan. 26, 2001.

CROSS-REFERENCE

Reference is made to U.S. patent application Ser. No. 10/060,052 entitled "Optical Detection In A Multi-Channel Bio-Separation System", concurrently filed on Jan. 28, 2002, now U.S. Pat. No. 6,828,567, which is commonly assigned to BioCal Technology, Inc., the assignee of the present invention, and which is fully incorporated by reference herein.

BACKGROUND OF THE INVENTION

1. Field of the Invention

The present invention relates to bio-separation, and more particularly a portable cartridge for supporting multi-separation columns with integrated detection optics and reagent reservoir and a bio-separation system incorporating the cartridge.

2. Description of Related Art

Bioanalysis, such as DNA analysis, is rapidly making the transition from a purely scientific quest for accuracy to a routine procedure with increased, proven dependability. Medical researchers, pharmacologists, and forensic investigators all use DNA analysis in the pursuit of their tasks. Yet due to the complexity of the equipment that detects and measures DNA samples and the difficulty in preparing the samples, the existing DNA analysis procedures are often time-consuming and expensive. It is therefore desirable to reduce the size, number of parts, and cost of equipment, to ease sample handling during the process, and in general, to have a simplified, low cost, high sensitivity detector.

One type of DNA analysis instrument separates DNA molecules by relying on electrophoresis. Electrophoresis techniques could be used to separate fragments of DNA for genotyping applications, including human identity testing, expression analysis, pathogen detection, mutation detection, and pharmacogenetics studies. The term electrophoresis refers to the movement of a charged molecule under the influence of an electric field. Electrophoresis can be used to separate molecules that have equivalent charge-to-mass ratios but different masses. DNA fragments are one example of such molecules.

There are a variety of commercially available instruments applying electrophoresis to analyze DNA samples. One such type is a multi-lane slab gel electrophoresis instrument, which as the name suggests, uses a slab of gel on which DNA samples are placed. Electric charges are applied across the gel slab, which cause the DNA sample to be separated into DNA fragments of different masses.

Another type of electrophoresis instrument is the capillary electrophoresis (CE) instrument. By applying electrophoresis in a fused silica capillary column carrying a buffer solution, the sample size requirement is significantly smaller and the speed of separation and resolution can be increased multiple times compared to the slab gel-electrophoreses method. These DNA fragments in CE are often detected by directing light through the capillary wall, at the components separating from the sample that has been tagged with a fluorescence material, and detecting the fluorescence emissions induced by the incident light. The intensities of the emission are representative of the concentration, amount and/or size of the components of the sample. In the past, Laser-induced fluorescence (LIF) detection methods had been developed for CE instruments. Fluorescence detection is often the detection method of choice in the fields of genomics and proteomics because of its outstanding sensitivity compared to other detection methods.

Some of the challenges in designing CE-based instruments and CE analysis protocols relates to sample detection techniques. In the case of fluorescence detection, considerable design considerations had been given to, for example, radiation source, optical detection, sensitivity and reliability of the detection, cost and reliability of the structure of the detection optics. In the past, a relatively high power light source is required, such as a Laser. When light is directed through the capillary wall at the separated sample components in the capillary bore, light scatters at the outside capillary wall/air interface and the inside capillary wall/buffer interface (Raman scattering), which obscures or corrupts the fluorescence emission intensity. Similarly, fluorescence emissions scatter at the wall interfaces. In the past, various techniques were developed for more completely collecting the fluorescence emissions to improve signal intensity and hence detection sensitivity. These techniques involve additional moving and non-moving components that add to the relative complexity and cost of the detection setup.

The design limitations of prior art electrophoresis instruments are exacerbated in the development of multi-capillary CE-based instruments. For example, confocal scanning laser induced fluorescence (LIF) detection has been adopted in multi-capillary electrophoresis systems. The scanning confocal detection relies on a scanning optical system. The use of moving parts is not ideal when taking simplicity, robustness, and lower cost of the instrument into consideration. Also, the shallow focal depth of the microscope objective for the confocal detector puts severe demands on the mechanical and optical component tolerances. Further, the optical scanning method generally involves a longer duty cycle per capillary. Thus, should the instrument be scaled up in order to generate higher throughput, the sensitivity of the system may be compromised. Also, another detection method is Sheath Flow detection. The main drawback of the sheath flow detector is the highly sophisticated flow system needed to ensure a reliable sheath flow with minimum optical cross talk between the channels. Extreme demands are put on the optical and mechanical component tolerances in order to meet the robustness demands of end-users. The sensitivity of the device is very good, but it is not obvious that this principle of fluorescence detection is suited for a high-throughput, yet low cost, DNA analysis.

Additional challenges in designing multi-capillary CE-based instruments related to the support of the capillaries. U.S. Pat. No. 5,198,091 to Burolla et al. describes a capillary cartridge for electrophoresis that employs a long length of capillary arrays. This patent may include a hollow space defined about the capillary for circulating coolant fluid but it does not include a reservoir as an integrated part of the cartridge. U.S. Pat. No. 5,413,686 to Klein et al. describes an automated multi-channel capillary electrophoresis analyzer including a plurality of capillaries. Reservoirs are shown in the analyzing apparatus, but they are multiple reservoirs and they are separated from the capillaries, not integrated into a capillary support. Detection optics are also shown in the apparatus, but they are not integrated into a compact capillary support. U.S. Pat. No. 5,338,427 to Shartle et al. describes a single use separation cartridge for a capillary electrophoresis instrument, in which capillary tubes are horizontally disposed in a coplanar array. The single use separation cartridge replaces large reagent reservoirs with hemispherical drops of reagent.

Also, current systems for gel buffer chemistry do not allow use of the CE instrument that is specific with applications. In other words, current CE instruments require matching the capillary (with different coatings and column sizes) with the buffer reagent for different separation applications (different types, speeds, resolutions).

SUMMARY OF THE INVENTION

The present invention provides a bio-separation system that uses an efficient, compact, simplified, portable, interchangeable, reusable, low cost, recyclable, easy to assemble multi-channel cartridge with no moving parts for bio-separation, which has integrated pre-aligned optics and an integrated reagent reservoir. The cartridge supports, for example, multiple capillaries for CE separation. The integrated reservoir containing a separation support medium (e.g., a gel buffer) is common to all capillaries. The chemistry of the medium and the characteristics of the capillaries (e.g., capillary size, coating and length) are defined for each cartridge. Different cartridges can be easily interchanged in the bio-separation system to suit the particular sample based separation. The reservoir is coupled to an air pressure pump that pressurizes the gel reservoir to purge and fill the capillaries with buffer as the separation support medium. In another aspect of the present invention, optics requiring fine alignment with respect to the detection zones (such as fiber optics for directing incident radiation or radiation emissions) are integrated into the cartridge.

In one aspect of the present invention, the cartridge supports multiple capillaries for CE separation. The cartridge includes assembled body parts, excitation fibers, capillaries, electrodes, a buffer/gel reservoir, and integrated optics for external radiation input. The reservoir is equipped with a single electrode common to all capillaries.

In another aspect of the present invention, optics are integrated into the cartridge. According to an embodiment of the present invention, the optical excitation system is integrated with the cartridge. The excitation system includes directing excitation light by excitation fibers to detection zone by coupling LEDs with micro-ball lenses. The excitation fibers are routed to a V-groove assembly adjacent to each capillary. According to another embodiment of the present invention, the optical detection system is engaged with the cartridge by a shutter mechanism. The detection optics for each of the capillaries, or the detection array, is coupled to a single photo-multiplier tube. The detection array includes collimating the emission light from the detection zone by using micro-ball lenses and detection fibers.

In a further aspect of the present invention, the present invention provides a bio-separation instrument that incorporates the multi-channel bio-separation cartridge of the present invention.

BRIEF DESCRIPTION OF THE DRAWINGS

For a fuller understanding of the nature and advantages of the invention, as well as the preferred mode of use, reference should be made to the following detailed description read in conjunction with the accompanying drawings. In the following drawings, like reference numerals designate like or similar parts throughout the drawings.

DETAILED DESCRIPTION OF THE PREFERRED EMBODIMENTS

This invention is described below in reference to various embodiments with reference to the figures. While this invention is described in terms of the best mode for achieving this invention's objectives, it will be appreciated by those skilled in the art that variations may be accomplished in view of these teachings without deviating from the spirit or scope of the invention.

The present invention is directed to a novel CE system and novel cartridge configuration in which incident radiation (e.g., from a laser or LED source) for detection of separated analytes is directed through the boundary walls of the detection zone or the separation column. For purpose of illustrating the principles of the present invention and not limitation, the present invention is described by reference to embodiments directed to capillary electrophoresis and radiation induced fluorescence.

Figure 1:
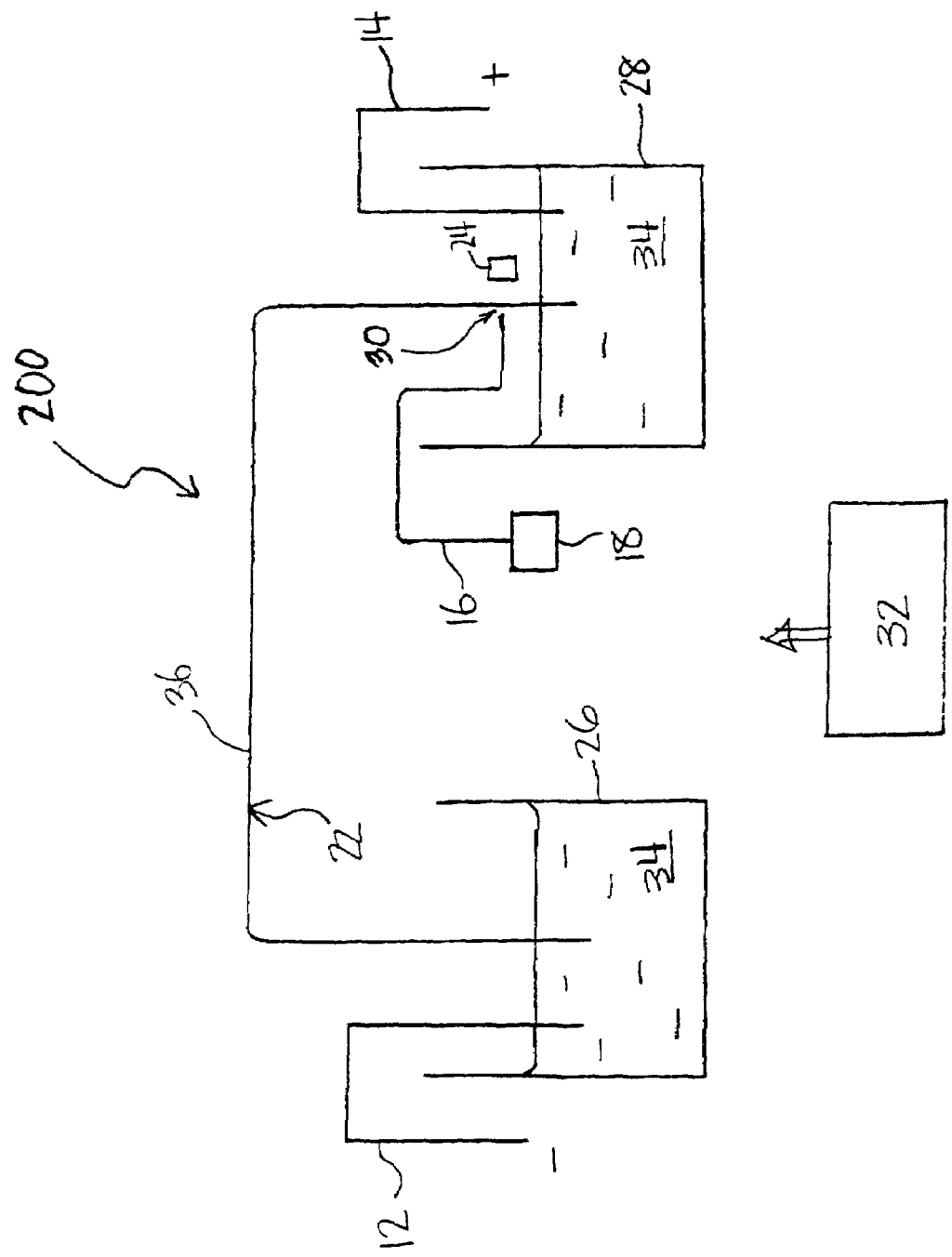
FIG. 1 is a schematic view of a capillary electrophoresis system that incorporates the present invention.

Referring to FIG. 1, a bio-separation system, more specifically a capillary electrophoresis (CE) system 200 that incorporates the present invention is schematically illustrated. The CE system 200 generally comprises a capillary separation column 22 (e.g., 200-500 μm O.D.), which defines a separation channel 36 (e.g., 25-200 μm I.D.). The capillary column 22 may be made of fused silica, glass, polyimide, or other plastic/ceramic/glassy materials. The inside walls of the separation column 22 (i.e., the walls of the separation channel 36) may be coated with a material that can build up an electrostatic charge to facilitate electrophoresis and/or electrokinetic migration of the sample components. The separation channel 36 is filled with a separation support medium, which may simply be a running buffer, or a sieving gel matrix known in the art. For radiation induced fluorescence detection, the gel matrix includes a known fluorophore, such as Ethidium Bromide.

One end of the capillary column 22 is submerged in a reservoir 28 of running buffer/gel 34. The other end of the capillary column 22 is coupled to the sample vial 26. It is understood that the detection configurations shown in the other embodiments can be equally implemented in a system similar to the CE system 20. Also, the separation channel 36 may be one straight capillary or micro-channel with a section of the detection window closest to the gel-reservoir at the exit end being the detection zone, which is the current preferred mode of our invention. A radiation detector 24 is positioned outside a transparent section of the capillary walls at detection zone 30. An excitation fiber 16 extends from a radiation source 18 (e.g., LED or laser) and is directed at the detection zone 30 outside the walls of the column. Electrodes 12 and 14, that are part of the cartridge assembly are coupled to the buffer reservoirs 26 and gel reservoir 28 to complete the electrophoresis path.

For the sake of completeness, it is sufficient to briefly mention the operation of the CE system 200. In operation, a prepared biological sample (e.g., a DNA sample), direct from Polymerase Chain Reaction (PCR) machine is introduced into the far end of the capillary column away from the detection zone by any of a number of ways that is not part of the present invention (e.g., electrokinetic injection from a sample reservoir or physical pressure injection using a syringe pump). The sample binds to the fluorophore.

When a DC potential (e.g., 1-30 KV) is applied between electrodes 12 and 14, the sample migrates under the applied electric potential along the separation channel 36 (e.g. DNA that is negatively charged travels through the sieving gel with an integrated dye matrix/fluorophore toward a positive electrode as shown in FIG. 1) and separates into bands of sample components. The extent of separation and distance moved along the separation channel 36 depends on a number of factors, such as migration mobility of the sample components, the mass and size or length of the sample components, and the separation support medium. The driving forces in the separation channel 36 for the separation of samples could be electrophoretic, pressure, or electro-osmotic flow (EOF) means.

When the sample reaches the detection zone, excitation radiation is directed via the excitation fiber 16 at the detection zone. The sample components fluoresce with intensities proportional to the concentrations of the respective sample components (proportional to the amount of fluorescent tag material). The detector 24 detects the intensities of the emitted fluorescence at a wavelength different from that of the incident radiation. The detected emitted radiation may be analyzed by known methods. For an automated system, a controller 32 controls the operations of the CE system 200.

Multiple Capillary Cartridge Based CE System

Figure 2:
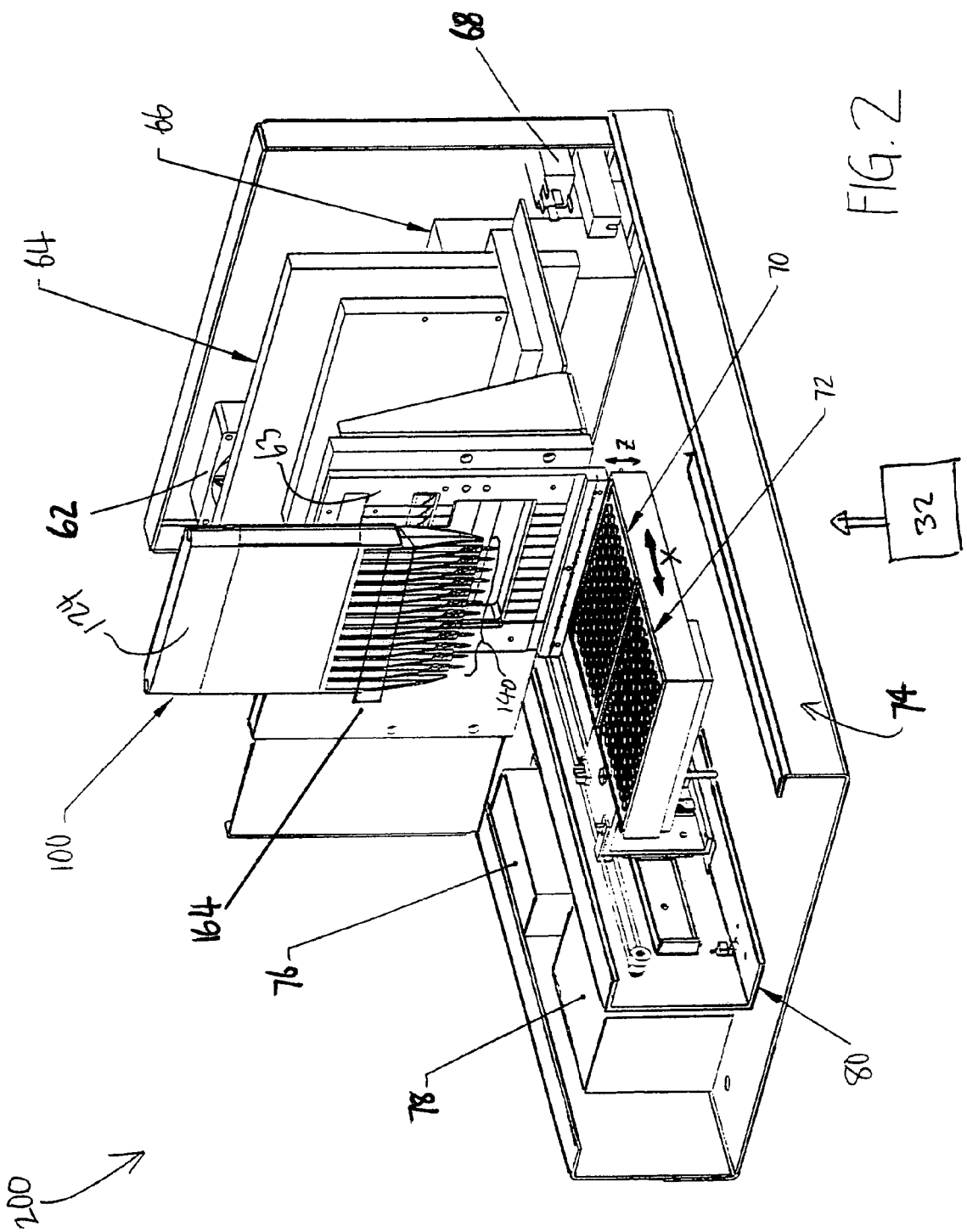
FIG. 2 is a perspective view of the capillary electrophoresis system/machine in accordance with one embodiment of the present invention.

The multi-channel capillary array includes twelve detection zones 30 defined by micro-channels 36 in cartridge body (also see FIG. 2). The substrate cartridge body may be machined, thermoformed, photo-etched or injection molded (e.g., Acrylic, PET, Ultem, Glastic, Fluorosint, or any optically clear plastic) to support the multi-channel capillary array to the integrated optics alignment V-grooves. The cartridge of the present invention includes a twelve-channel fused silica capillary array (16 cm long) that is used for separation and detection of the samples as part of a disposable cartridge assembly. When the cartridge is attached to the CE system in which it is designed for use, excitation fibers (i.e., multi-mode silica or plastic fibers, 0.22 N.A.) that are integrated with the micro-channels 36 are directed at the detection zone 30. Each channel is coupled to an LED. LED light is launched into the side of capillaries 36. In this particular embodiment, sieving gel fills the micro-channels/capillary array 36.

FIG. 2 shows the design of a multi-channel cartridge 100 installed in a CE system 200 in accordance with the one embodiment of the present invention, which provides easy handling of multi-channel separation columns, and allows easy optical coupling of the detection zones to the detection optics of the CE instrument. FIG. 2 shows an overall perspective view of the CE instrument 200 (DNA Analyzer) with the twelve-capillary cartridge in place. The fully automated DNA analysis instrument 200 has a base 74, supporting a modular X-Z sample handling tray mechanism 80, which moves two 96-well micro-titer plates 70 and 72 in relation to the multi-capillary cartridge 100 supported on support bracket 164. The system 200 provides easy handling of multi-channel separation columns, and allows easy optical coupling of the detection zones to the detection optics of the CE instrument 200.

The cartridge 100 described in greater details below. Briefly, the cartridge 100 includes a twelve-channel fused silica capillary array that is used for separation and detection of the samples as part of a disposable and/or portable, interchangeable cartridge assembly 100. The multi-channel capillary array includes twelve detection zones defined by micro-channels in the cartridge 100. The multi-channel cartridge 100 shown in FIG. 2 holds up to 12 capillaries 140, 12-16 cm long. The multi-channel cartridge 100 is integrated with a top, outlet buffer reservoir 124 common to all capillaries 140, which is directly coupled to a modular air pressure pump 78. The pressure pump 78 provides the required air pressure to fill-up all the 12-capillaries with the sieving gel contained in the reservoir 124 and to purge the gel from the previous run from the capillaries during the refilling process. Depending on the viscosity of the gel, pressures of up to 40 PSI may be applied to the capillaries 140 through the gel-filled reservoir 124. The cartridge gel-reservoir 124 is equipped with built in common electrode (anode; not shown) for all 12-capillaries, which is automatically connected to a high voltage power supply 76 for electrophoresis when installed inside the instrument 200. A fan or Peltier cooler on the adjacent structure to the cartridge 100 provides temperature control of the cartridge. The cartridge will have vent holes (input and output) for air circulation (temperature controlled air to be introduced to the cartridge from the instrument side). A power supply 66 provides DC power to the CE system 200.

Figure 3:
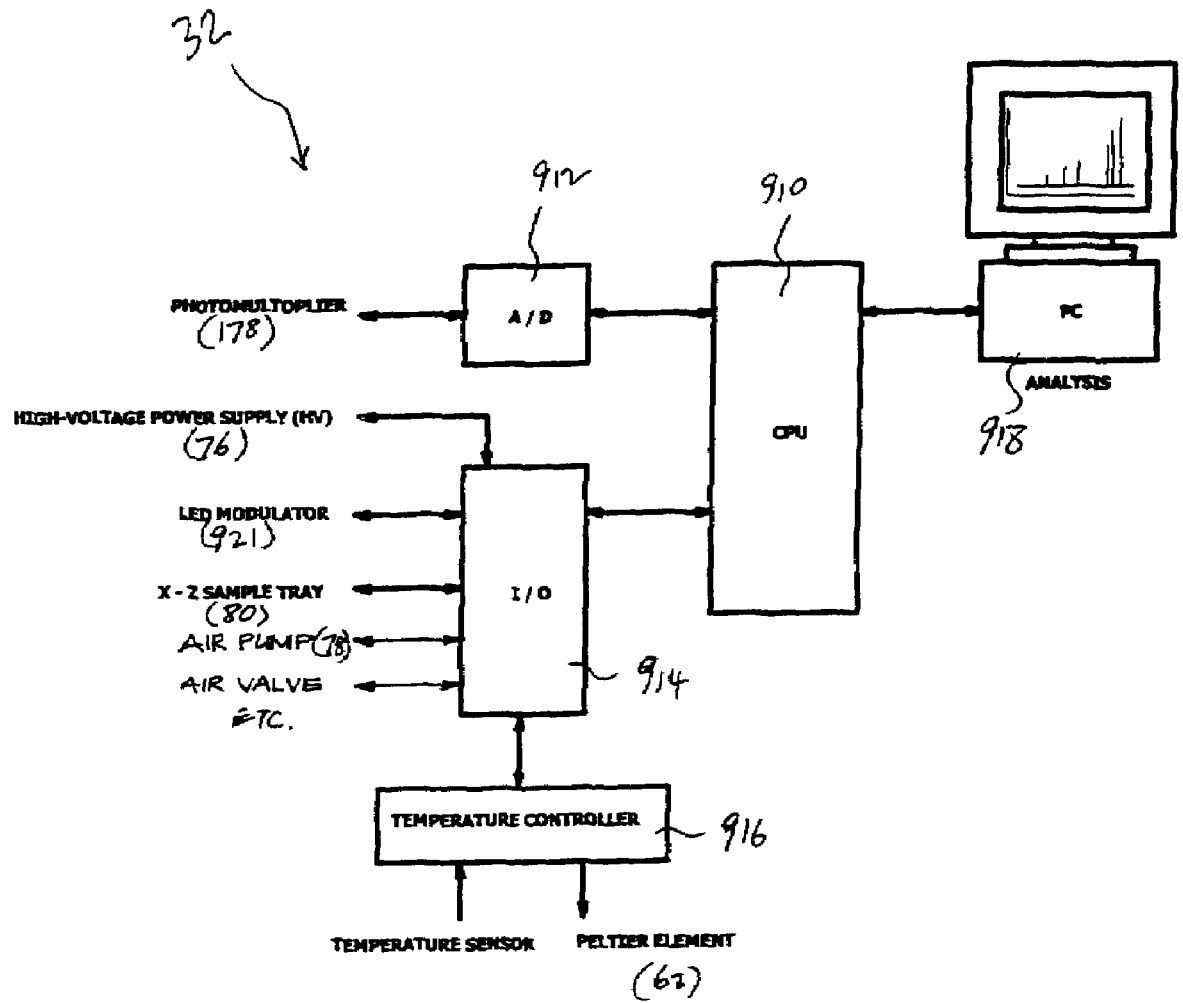
FIG. 3 is a diagram of the control system.

In accordance with one embodiment of the present invention, the block diagram of the controller 32 for the CE system 200 is shown in FIG. 3. The controller comprises a CPU 910, an A/D converter 912 for converting detection signals from the PMT 178 (FIG. 13) to corresponding digital signals, and an I/O interface 914 for transferring and receiving signals to and from respective parts of the CE instrument 200 by instructions from the CPU 910. A temperature controller 916 controls the fan or Peltier cooler 63 that controls the temperature of the electrophoresis chamber for the micro-channel/capillary array cartridge 100. The I/O interface 914 is coupled with the temperature controller 916, which also controls the high-voltage power supply 76 for sample injection and electrophoresis functions of the CE instrument 200, a circuit 921 for modulating the excitation radiation source (e.g., LEDs), sensors, air pump, air valve, and motors for the X-Z stage of the CE instrument 200. The CPU 910 may be further coupled to an external personal computer 918, which in turn performs data processing or additional control function for the CE system 200. The CPU210 and/or the PC 918 may be programmed with control functions dictated by LabVIEW™ software available from National Instruments Corporation, to control various features and functions of the automated multi-channel DNA analyzer 200.

The components of the controller 32, with the exception of the PC 218, may be packaged as an electronic board 64 (FIG. 2) and cooling fan 62, on board the CE system 200 and electrically coupled to the PC 218 via a serial port (not shown), or they may be part of a separate controller module outside of the CE system 200. The CPU 210 and/or the PC 218 are programmed to accomplish the various control functions and features for the CE system 200. In one embodiment, the PC 218 can be configured to provide the front panel control (i.e., user interface) for the instrument 200, and the board 64 may be configured to provided the time staggered/time multiplex detection controls. It would be within a person skilled in the art to implement the program code given the functions and features disclosed herein. An A/C power filter/switch 68 (FIG. 2) is provided for the instrument 200.

Injection of the samples is achieved by electrokinetic methods. The high voltage power supply 76 is used to deliver 0-to-20 KV of electrical field to the gelfilled capillaries for the electrokinetic injection and separations of DNA fragments. Each of the 12-LED's broad band light energy (FVHM=47 nm) is relayed by individual light transmitting optical fibers (multi-mode silica or plastic 200 micron Core fibers, 0.22 N.A.) to each of the capillary's detection zone inside the cartridge 100 for the excitation of the separated DNA fragments.

In operation, the sample handling tray transport mechanism 80, with a 96-well plate (8×12), is used to introduce the amplified DNA samples (or analytes) to each microbore channel 36. Inside the micro-channels 36 are Polyimide coated or glass capillary tubings 22 of smaller inner diameter (25-100 μm) used as separation columns. The X-Z transport mechanism 80 indexes a row of sample carrying wells under the row of capillary tips and dip the tips into the well. By applying a voltage, electrokinetic injection moves a known amount of the DNA sample to the beginning of the separation column 140. After injection, the DNA samples from sample tray 72 maybe replaced with a running buffer from tray 70. Alternatively, after injection, the transport mechanism 80 may index to move a row of 12 wells containing buffer solution into position under the cartridge to replace the twelve wells containing DNA samples. By applying high voltage across the total length of the capillary separation channel and the micro-channel 36, separation of the DNA sample into DNA fragments is achieved. Up to 1000 V/cm (typically 300 V/cm) of high voltage is applied, which provides fast separations of less than 10 minutes along the entire length of the separation channel. The total separation length is about 12.5 cm up to the detection zone. The separation capillary length inserted inside the micro-channel is about 6.5 cm. High voltage is applied to a total active length of 16-17 cm, which could be the length from the bottom to the top of one single capillary with 75 micron I.D. inside the gel-reservoir as a single separation and detection capillary. During electrophoresis, the rate at which the DNA fragments move through the sieving gel is inversely proportional to their mass; i.e., lighter (or smaller) DNA fragments move more quickly than heavier (or larger) ones. As the fragments approach the end of the separation column 22 and enter into the detection zone 30, the excitation light energy from each of the twelve LEDs (not shown) is delivered by individual light transmitting optical fibers from outside the detection window, illuminating the migrating DNA fragments from sample tray 72. As the DNA fragments move through the sieving gel, or linear polymer solution (e.g., 25 mM Mops-Tris pH 7.55, as referenced in "Pace Setter", Vol. 3, Issue 1, Apr. 1999), a DNA intercalating dye (Ethidium Bromide) within the sieving gel allows the migrating DNA fragments to be detected. Experiments have shown that detection sensitivities of 100 ng/ml (0.02 ng of the Haelli digest φX174 DNA test mix) are achievable, which is several orders of magnitude better than conventional slab gel electrophoresis devices using the same intercalating dye. As the twelve LEDs are time-multiplexed (with sampling frequency of 10-100 Hz), twelve emission signals coupled to twelve emission detection fibers will reach the single PMT in a time-staggered manner by a single fiber-bundle assembly.

To prepare for the next run with a different sample, the old gel from the previous run is purged from the capillaries by pressuring the reservoir to refill the capillaries with fresh gel. The trays 70 and 72 carries cleaning solutions, waste collection, and samples. The purged gel is collected by one of the trays 70 and 72 by positioning the tips of the capillaries at a row of waste collecting wells in one of the trays. The tips of the capillaries may be cleaned with water or a cleaning solution by positioning and dipping the tips of the capillaries in such solution in the appropriate tray wells. When the capillaries are refilled and ready for the next run, the tips of the capillary are dipped into the samples by repositioning the trays 70 and 72. The above mentioned sequence of process may be programmed as one of the automated functions of the controller 32.

It is noted that because the sample analytes that flowed to the gel reservoir at the exits of the capillaries are in such small amount and volume concentration compared to the volume of the reservoir, and that the analytes are expected to be mixed within the gel reservoir, there will only be a negligible trace of analytes from past runs in the reservoir, and that will be evenly distributed in the gel that refills the capillaries for the next run. Any noise from this negligible trace would be relatively small background noise that can be easily removed from the detected signal in the data analysis.

Figure 4:
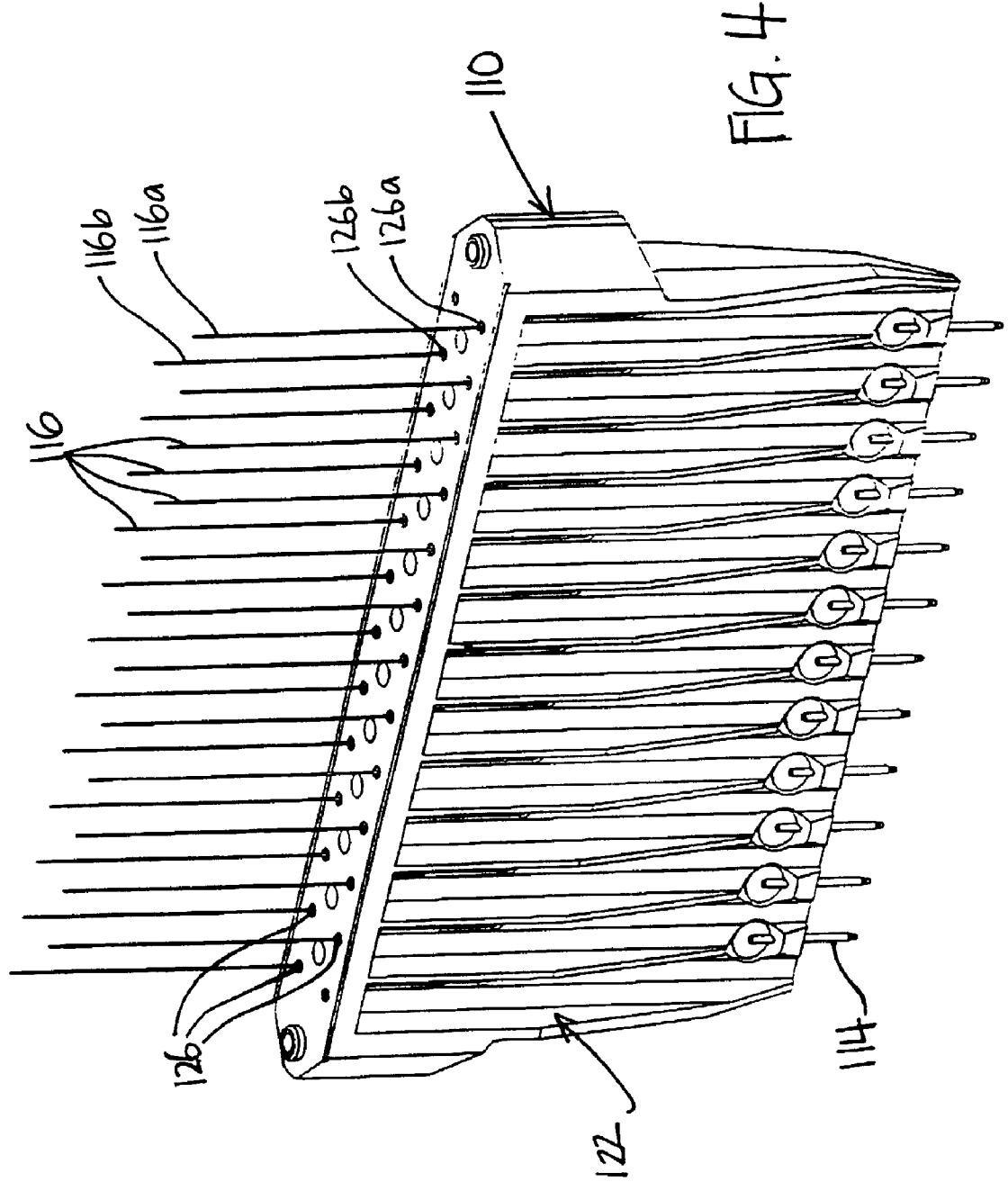
FIG. 4 is a perspective view of the cartridge lower section with excitation fibers.

FIGS. 4-9 show the steps for assembling components for the cartridge. They are described here for illustrative purposes and are not to be taken in a limiting sense. FIG. 4 shows the lower section body 110 of the cartridge 100. At the upper end of the lower-section body 110 are openings 126 through which portions of the excitation fibers 116 are placed; after being placed through these openings, the excitation fibers 116 are bonded in place. (Other means of securing these components may be used as well.) At the lower end of the lower-section body 110 are electrodes 114 that are also bonded (or insert molded as part of 110). The capillaries 140 (FIG. 7) are inserted at holes 139 and guided to these electrodes 114. For a twelve-capillary cartridge, there are twice as many excitation fibers (i.e., twenty-four excitation fibers, in case of upgrading for dual-wavelength type detections). These excitation fibers 116 are positioned to alternate around the twelve capillaries 140. This is seen more clearly as fiber openings 126a and 126b may be used for excitation fibers 116a and 116b (FIG. 4) for capillary 140, respectively.

Figure 5:
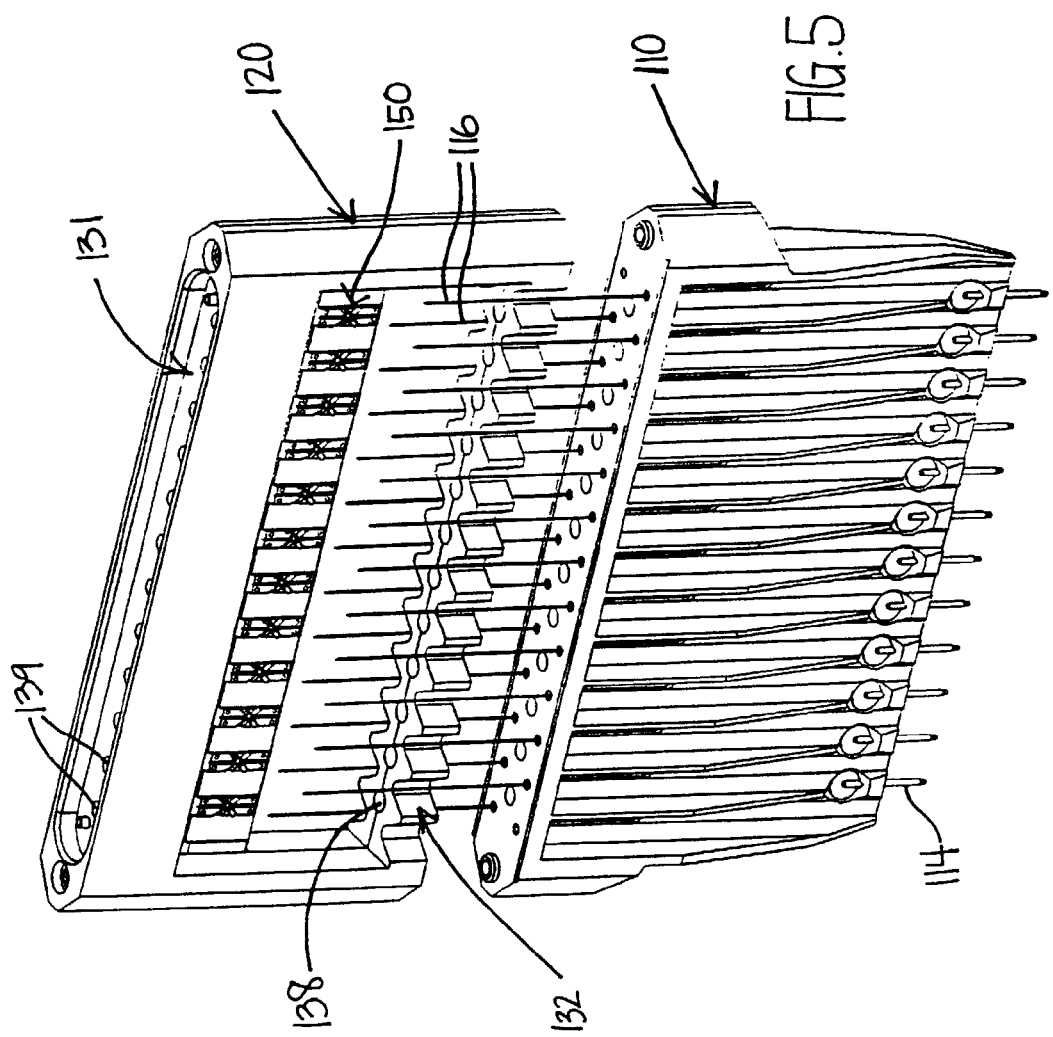
FIG. 5 is a perspective view of the cartridge mid-section and the lower section with excitation fibers before being joined.

FIG. 5 shows the addition of the cartridge mid-section body 120 to the lower-section body 110 in FIG. 4. The cartridge mid-section body 120 is designed so that the part 132 does not obstruct the path of the excitation fibers 116 or that of the capillaries 140. The part 132 has a zigzag design that does not enclose the excitation fibers 116 and that is generally horizontal-while the cartridge is in operation. This part 132 also has holes 138 through which the capillaries 140 are placed, as will be shown in further figures. The top end 131 of the mid-section body 120, which will form part of the reservoir, also has holes 139 through which the capillaries 140 will be placed.

Figure 6:
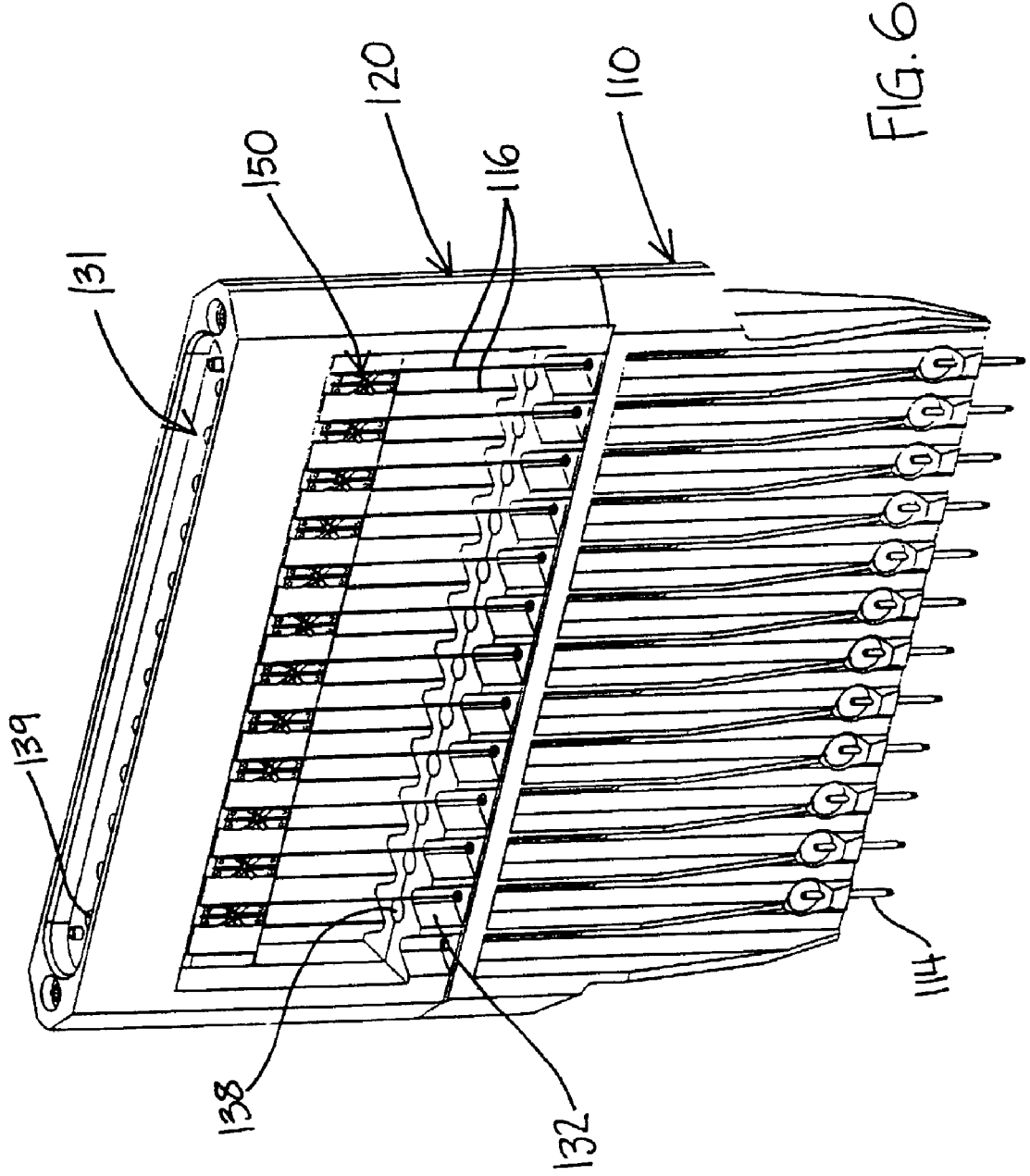
FIG. 6 is a perspective view of the cartridge mid-section and the lower section with excitation fibers after being joined.
Figure 7:
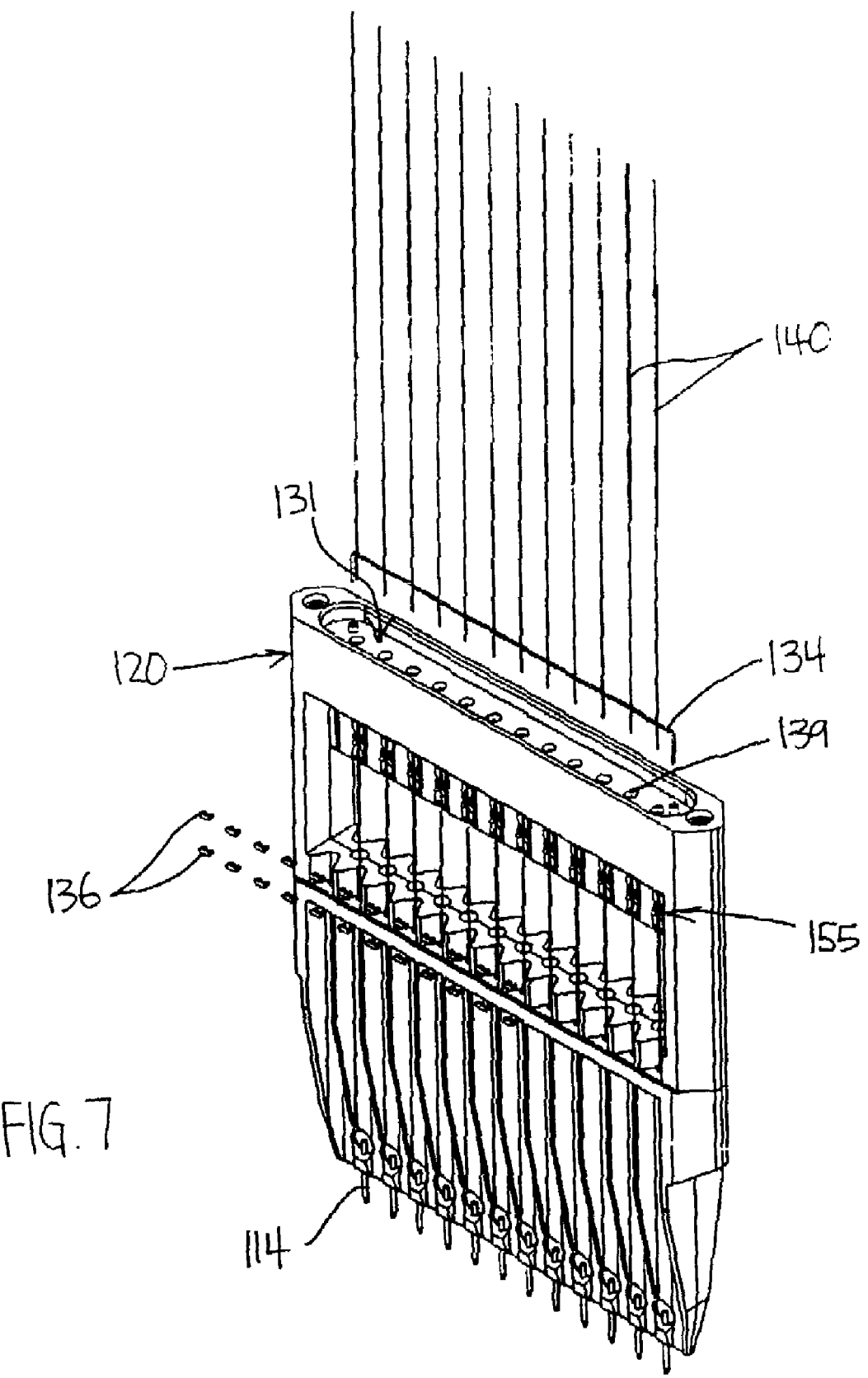
FIG. 7 is a perspective front view of the combined cartridge mid-section and the lower section in FIG. 6 with capillaries before being joined.

After the mid-section body 120 of the cartridge is mounted onto the lower-section body 110, as shown in FIG. 6, polyimide coated capillaries 140 are placed through the capillary holes 139 and 138 until they reach the lower end of the lower-section body 110 (see FIG. 7). The capillaries 140 have a pre-burned window, with the polyimide coating removed to provide a detection window. Staples 136 may be used to secure the capillaries 140 to the mid-section body 120 of the cartridge. At the top end 131 of the mid-section body 120 is a common electrode (anode) 134 for the capillaries that extends into the reservoir.

Figure 8:
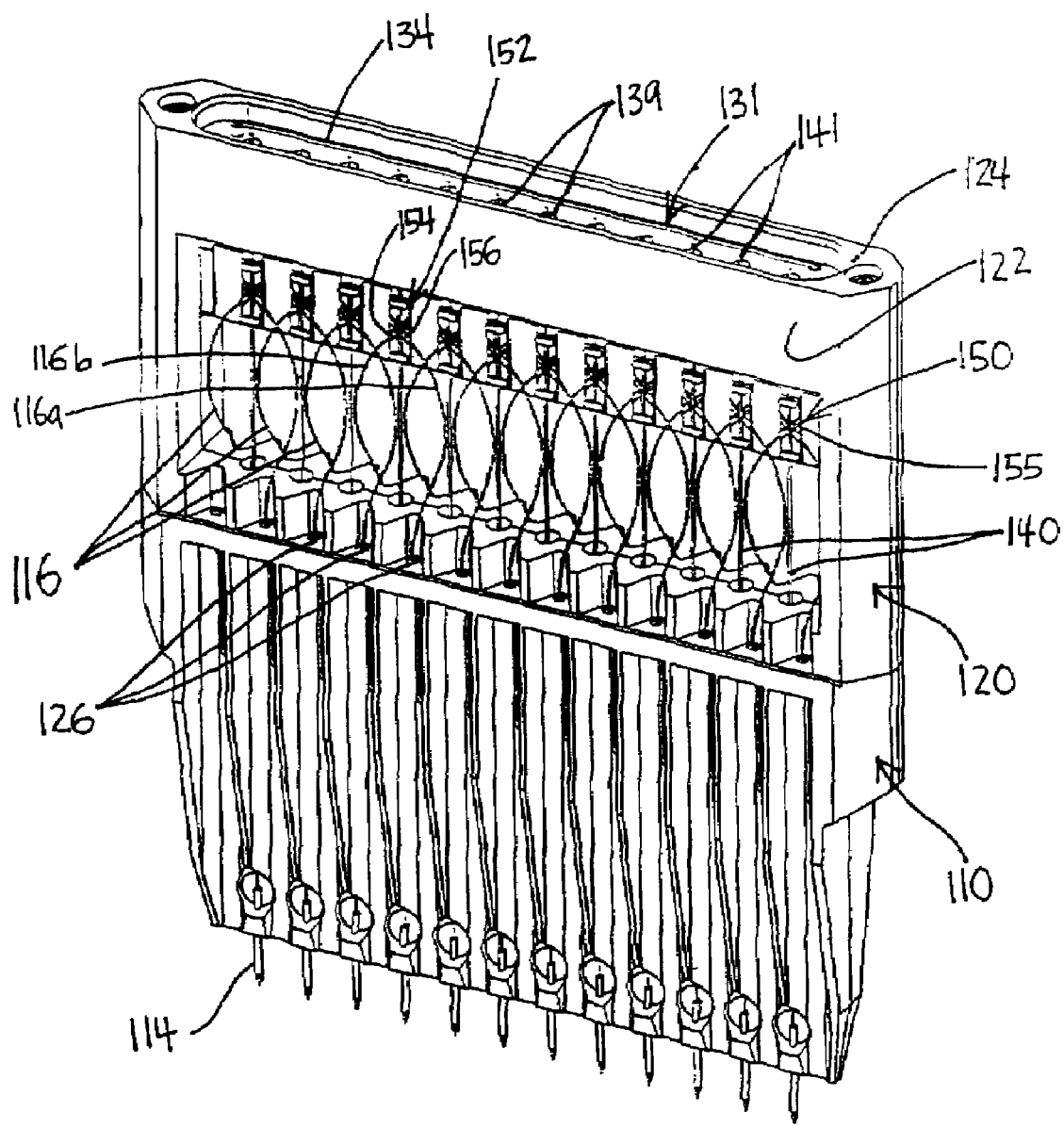
FIG. 8 is perspective front view of the cartridge mid-section and lower section with capillaries after being joined.

FIG. 8 shows the cartridge with the combined mid-section and lower-section bodies 110 and 120, respectively. The capillaries extend from the top of the mid-section body 120 (with the capillary tips 141 protruding at the opening 131 for the reservoir) to the bottom of the lower-section body 110 with the electrodes (cathodes) 114. The detection zone 155 of the capillaries is also shown. The excitation fibers 116 are shown through fiber openings 126 (see also FIG. 4) up to the V-groove block assembly 152, where light from the excitation fibers is directed at the capillaries.

Figure 9:
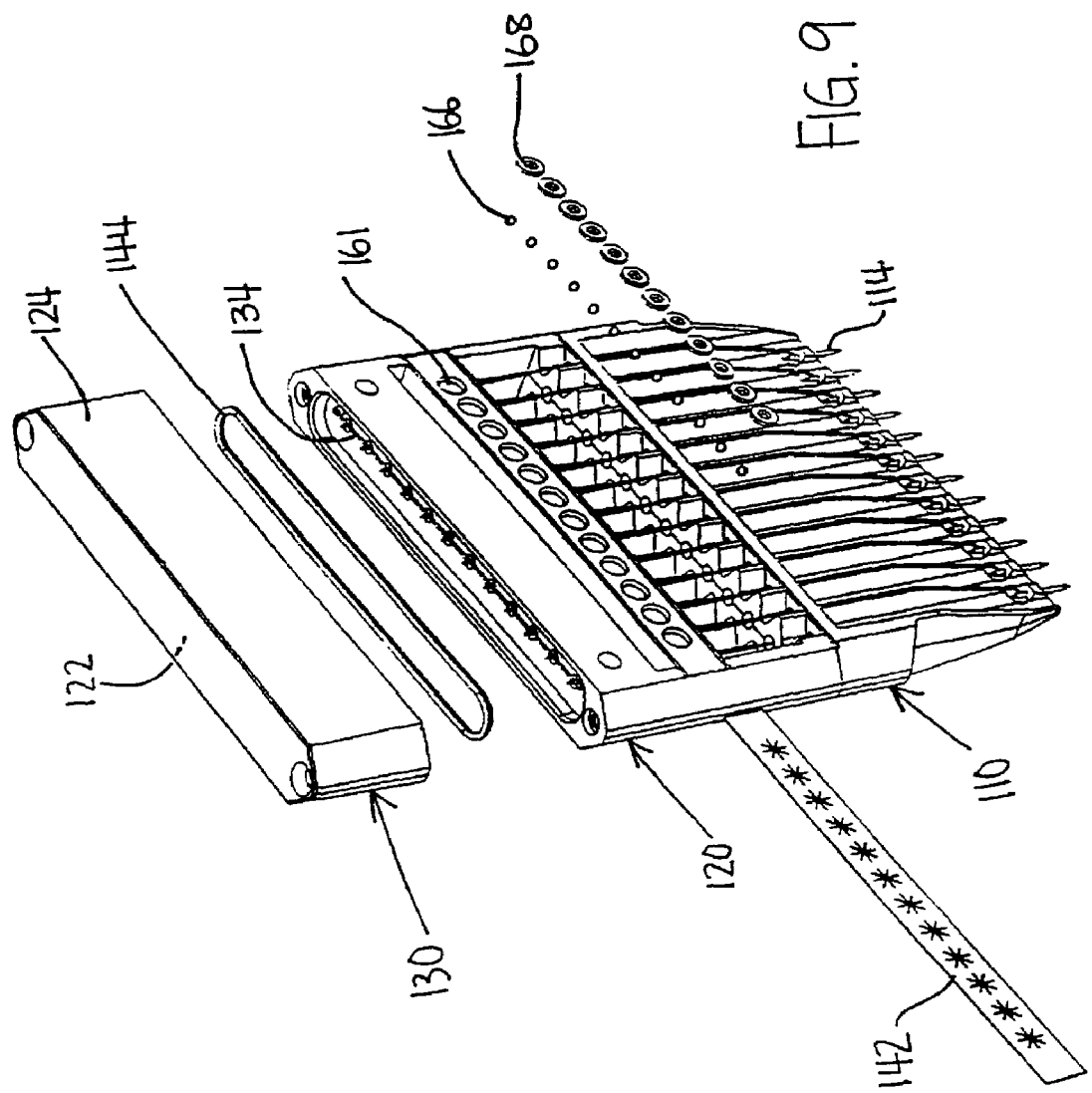
FIG. 9 is a perspective rear view of the cartridge mid-section and lower section with the gel reservoir.

In FIG. 9, a rear view of the cartridge is shown. The cartridge is integrated with a top/outlet buffer reservoir 130 common to all capillaries. The gel reservoir 130 is attached to the mid-section body 120 with an O-ring 144 as a seal. The gel reservoir 130 has a capacity of about 18 cc and may have transparent, or clear, windows on each side for inspection of the gel level. The gel reservoir 130 is coupled to a modular air pressure pump 78 (see also FIG. 2). The pressure pump 78 provides the required air pressure to fill all 12-capillaries with the sieving gel. Depending on the viscosity of the gel, pressures of up to 40 PSI have been applied to the capillaries through the gel-filled reservoir. The cartridge 100 has a single electrode (anode) 134 at the top opening of the mid-section body 120 and multiple electrodes (cathodes) 114 at the lower-section body 110 as part of the cartridge assembly. The cartridge gel reservoir 140 is equipped with a built-in electrode (anode) 134 common for all twelve capillaries, which is automatically connected to the high voltage power supply 76 via off the shelf pogo-pins for electrophoresis when installed inside the instrument 200 (DNA Analyzer). A commercially available high voltage power supply (i.e. Emco) is used to deliver 0 to 20 KV of electrical field to gel-filled capillaries 140 for the electrokinetic injection and separations of DNA fragments.

The reservoir 130 containing the gel is sealed, such as hermetically sealed at the body of the cartridge, which allows the cartridge to be handjed by holding it in any orientation without leakage of the gel. (There is negligible leakage or exposure at the capillary tips because of surface tension and high viscosity within the microbore of the capillaries.) The cartridge 100 has a rubber septum (not seen) that is pierced by an instrument-mounted needle (or any sharp object) that provides air pressure from the pump 78 into the cartridge. This allows air pressure to fill the capillaries with the gel/buffer solution after each separation run, and to purge the old gel from the previous run in the process. This approach assures the proper containment of the gel inside the cartridge reservoir; it also provides a simple and reliable means of accessing the gel reservoir and of providing enough air pressure for the gel to fill up the capillaries prior to applying high voltage to effect CE separation.

The cartridge 100 also has detection optic ports 161 through which detector probes 170 (FIG. 11) are fitted. Through each of these detection optic ports 161, microlenses 166 for emission collection optics are placed, followed by elastomer lens retainers 168. The cartridge also has a shutter covering, or a multi-channel aperture strip 142, at the detection optic port 161. The aperture strip 142 may be a thin Polyester material about 0.5 mm thick, which will prevent any dust particles or foreign objects from entering inside the collection optics area. The apertures 142 will open up when the detection array 170 containing the collection optics enters the cartridge. The apertures 142 will close up again when the detection array 170 is removed from the cartridge assembly. The shutter can also be a mechanical covering or window, which opens up when it is interfaced with the instrument's detection optics.

Figure 10:
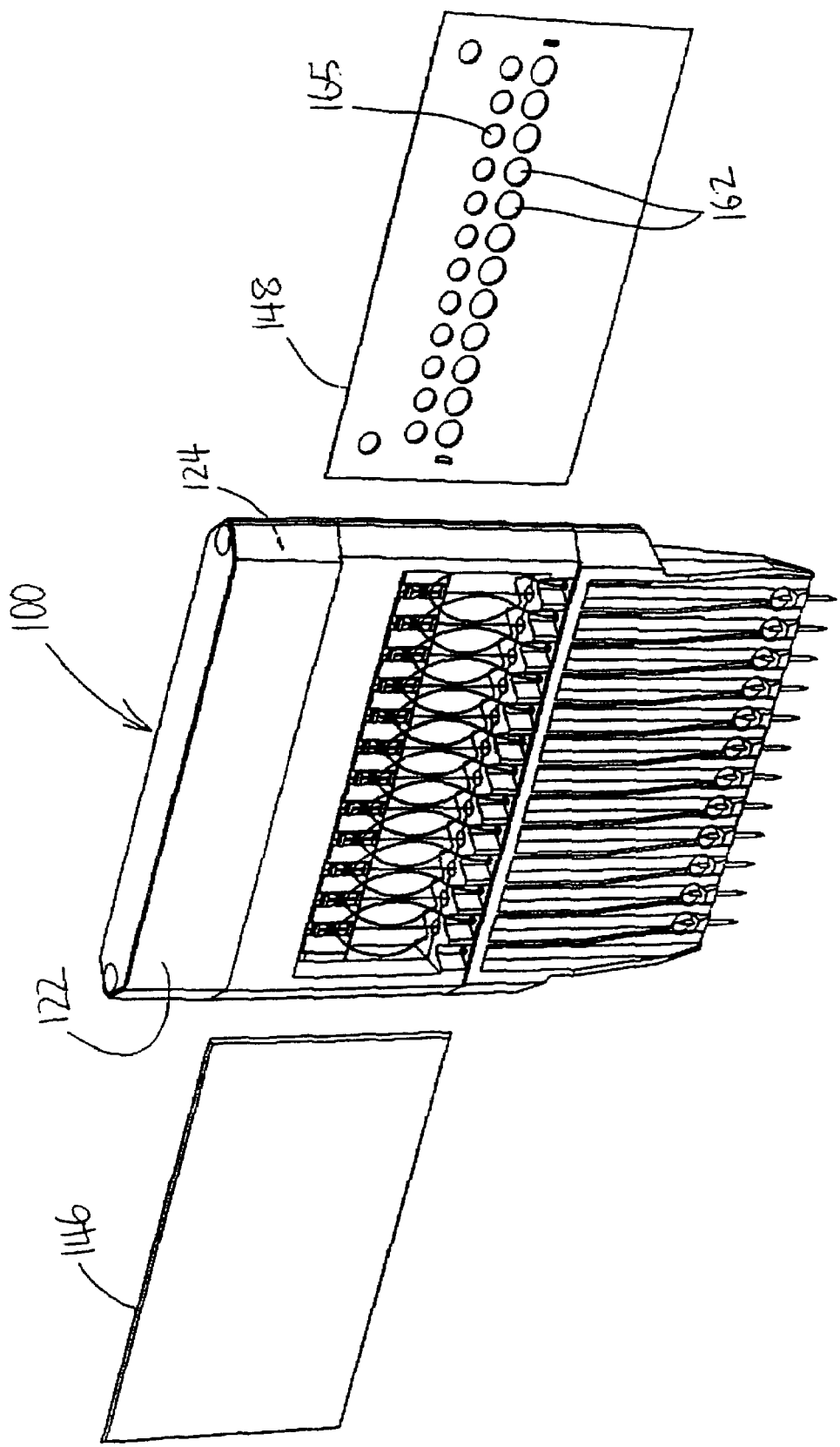
FIG. 10 is a perspective front view of the cartridge mid-section and lower section with the gel reservoir and front and rear covers.

The last stage of assembling the cartridge is shown in FIG. 10 with the front cover 146 and the rear cover 148. The rear cover 148 has holes 162 for each of the detection optic ports 161. There are also vent holes 165 above holes 162 through which cooled air flows inside the cartridge to cool the capillaries.

Figure 11:
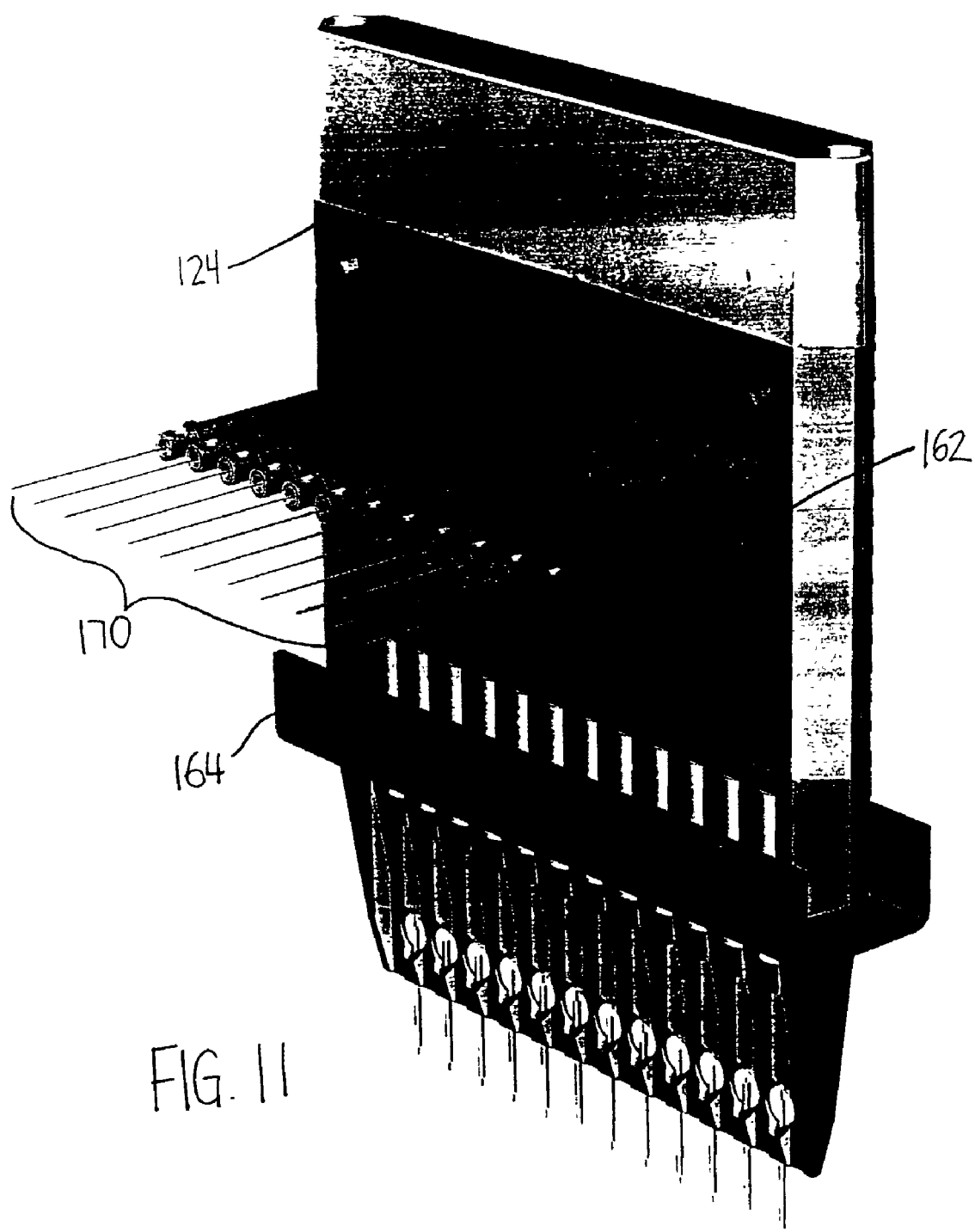
FIG. 11 is a front perspective view of the cartridge with detection optics inserted.
Figure 12:
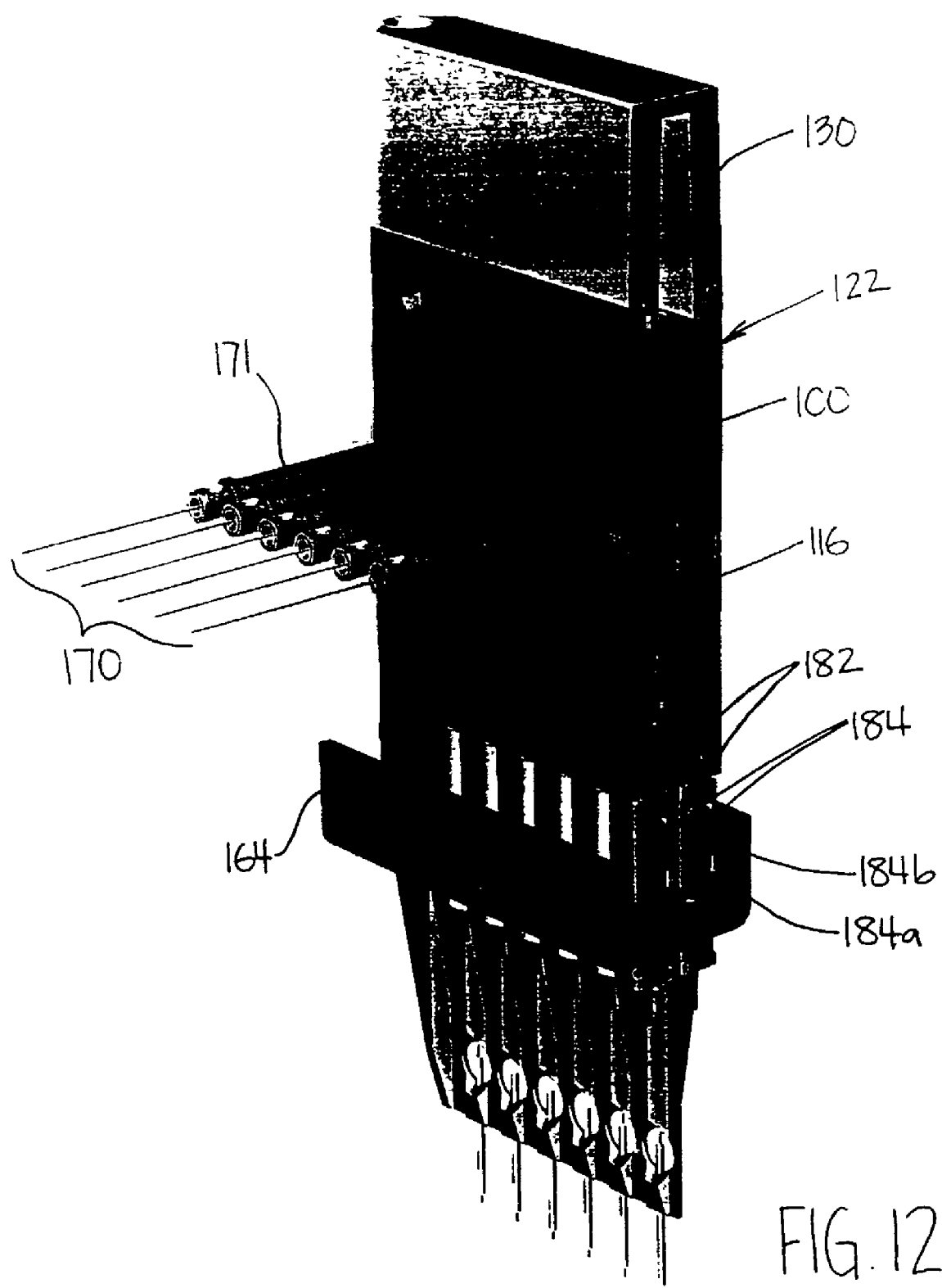
FIG. 12 is a front perspective sectional view of the cartridge in FIG. 11 with the excitation and emission optical system.
Figure 13:
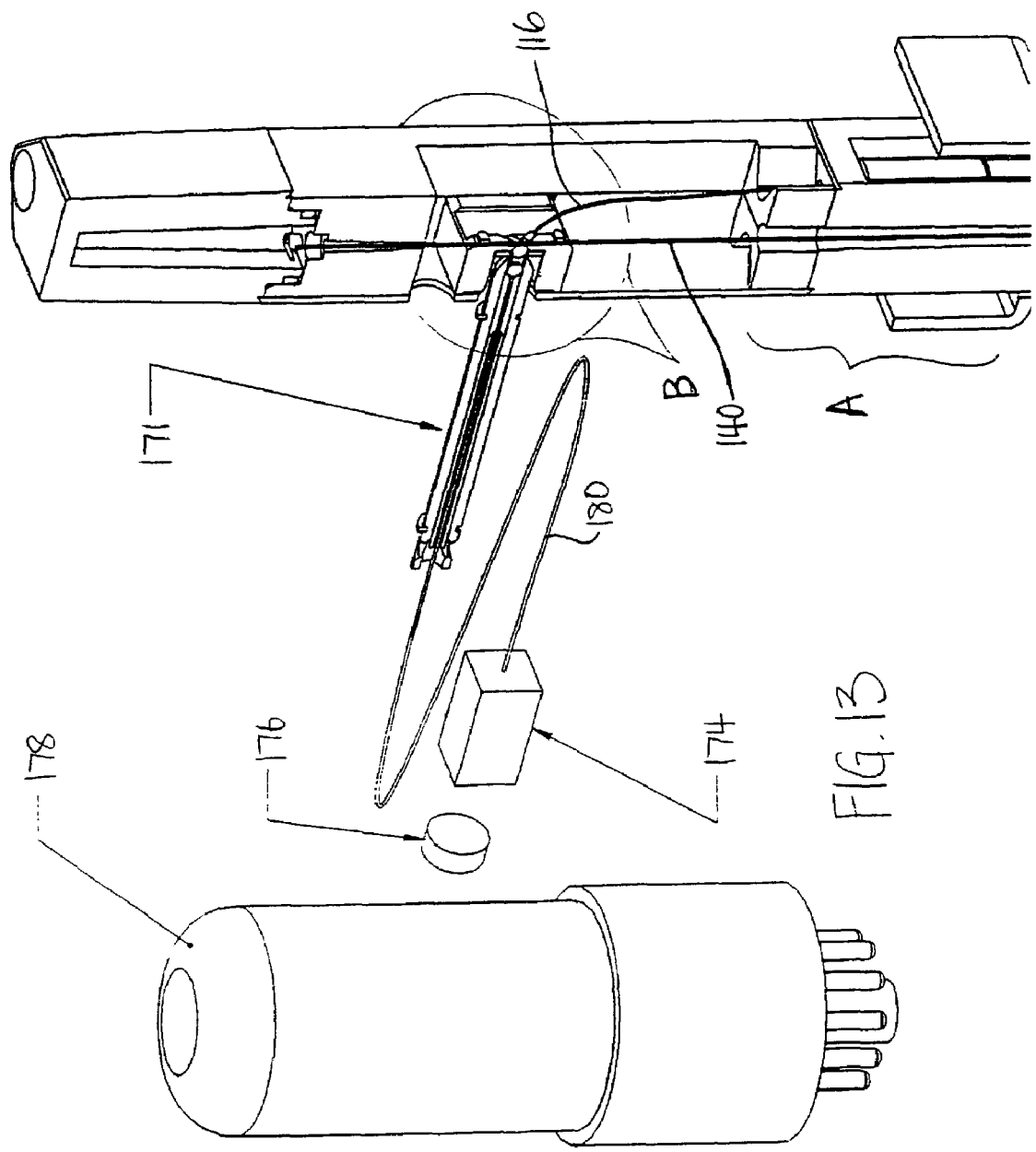
FIG. 13 is a perspective sectional view of the cartridge with schematic of the detector system.

FIGS. 11 and 12 show the rear view 124 of the cartridge 100 with a clearer view of the emission collection fiber array 170. FIG. 12 shows that the lower-section body 110 is symmetrical, front and rear (i.e., see mirrored LEDs 184a and 184b). FIG. 13 shows a perspective sectional view of the cartridge 100 with a detector probe 171 from the emission collection optical detection array 170 coupled to a single photo-multiplier tube (PMT) 178 through a fiber connector 174 and an emission filter 176.

Figure 14:
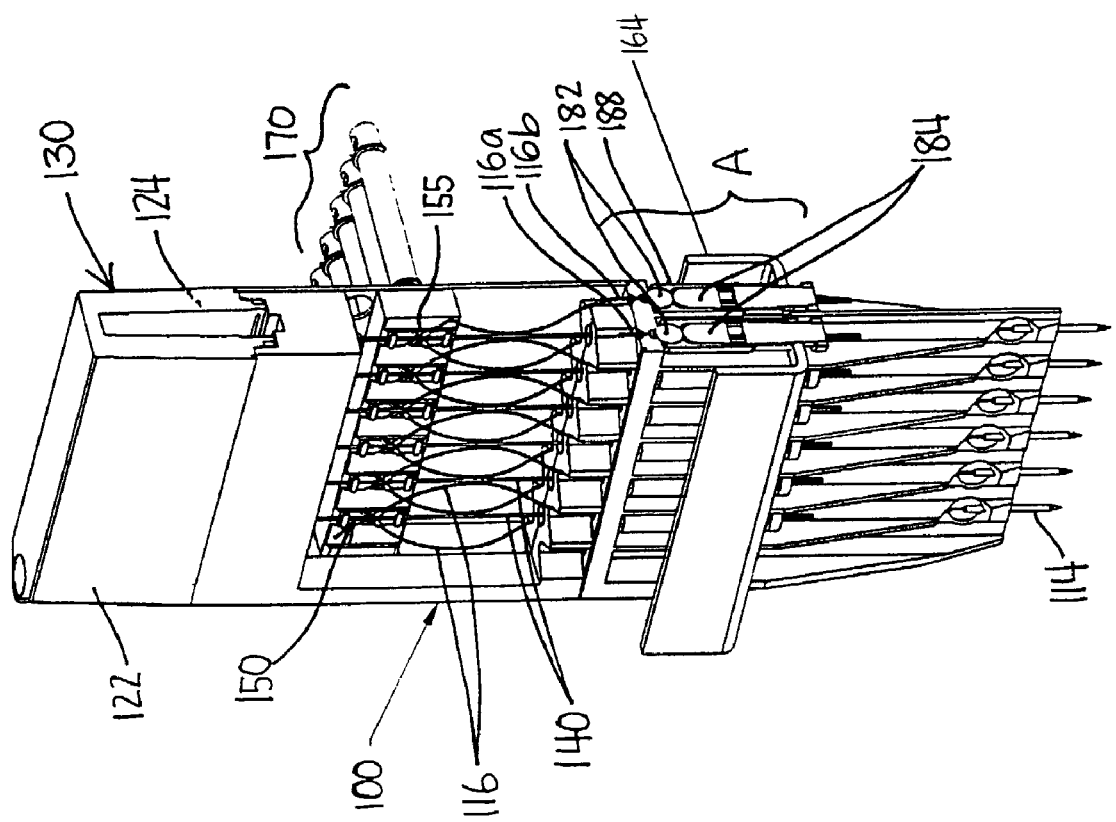
FIG. 14 is a front perspective sectional view of the cartridge with the excitation and emission optical system.

FIG. 14 shows a sectional view of the cartridge 100 along with the excitation and emission optical systems. The cartridge 100 is supported by support frame 164. The cartridge when installed inside the instrument through this support frame 164 gets mechanically aligned with LED module/barrel assemblies. The structure of the lower body of cartridge 110 provides the optical alignment means or coupling of lens barrel assembly 188 to the excitation fibers inside the cartridge. The excitation system includes the coupling micro-ball lenses 182 with respective LEDs 184. The excitation light from the LEDs 184 is directed through the excitation fibers 116 to the detection zone 155 of the capillaries. The emission system includes the emission collection fiber array 170, which is connected at the rear side 122 of the cartridge 100.

The cartridge has alignment features to be easily aligned to the micro-optical detection module inside the instrument 200. The optical detection array 170 and LED array 184 are all spring loaded, which provides independently compliant forces to each lens barrel assembly 188 (i.e. LED or fiber ferrule) for a reliable and repeatable alignment to the cartridge. The cartridge has all the proper conical type features (i.e., conical lens seating 186) to accept the spring and the spring loaded arrays from the instrument, as will be described in greater detail below.

Excitation System

Figure 15:
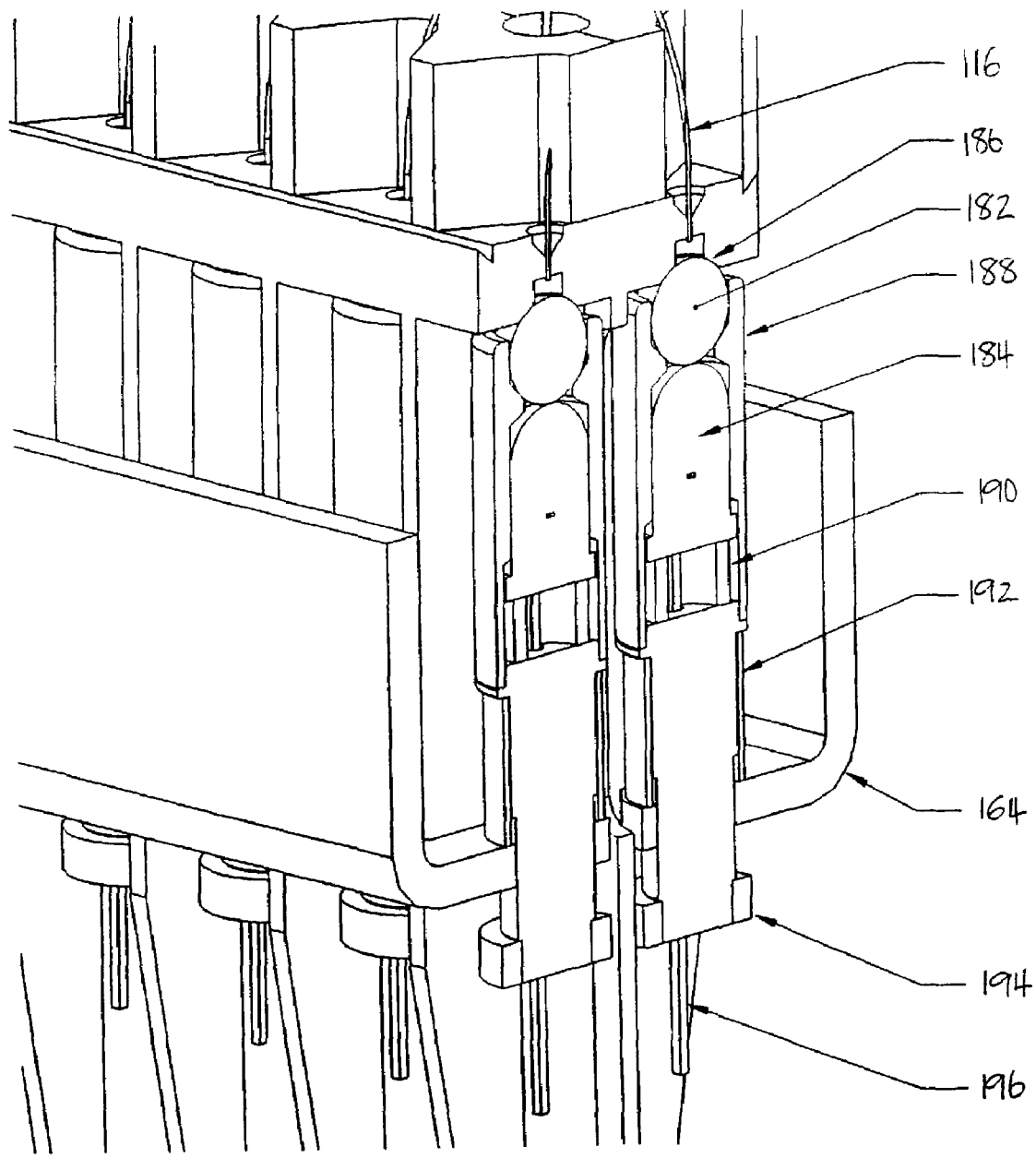
FIG. 15 is an enlarged view of section A in FIG. 14 and a perspective sectional view of the cartridge section A shown in FIG. 13.

A closer look at section A in FIG. 14 shows the excitation system in FIG. 15. This also shows an angled sectional view of the cartridge section A in FIG. 13. The excitation system is supported by the excite support frame 164, which is fitted to the cartridge (in FIG. 10) during use (as shown in FIG. 11). Since the excitation fiber 116 must receive light and direct light along its path toward the capillary detection zone 155, the excitation system is configured to allow the required light to enter excitation fiber 116 through a ball lens 182 from LED 184. The excitation system includes ball lens 182, LED 184, and elastomer spring 190, which are all arranged within lens barrel 188, coil spring 192, excite support frame 164, retainer 194, and LED lead 196. Within the lens barrel 188, the elastomer spring biases LED 184 against ball lens 182. The coil spring 192, which rests on the excite support frame 164, provides axial and angular compliance in the lens barrel 188, thus allowing ball lens 182 to center accurately in conical lens seat 186. Both these biasing forces provide a closer contacting path for the excitation light to travel, from the LED 184 through the ball lens 182 to the excitation fiber 116.

Two excitation fibers 116 for two wavelengths (for each capillary) are integrated inside the cartridge 100, with fixed alignment, at close proximity to the capillary detection zone 155. These two excitation fibers 116 are coupled to two LEDs 184 (e.g., two different colors: 526 nm and 473 nm) when the cartridge is installed inside the CE instrument 200 (i.e., DNA Analyzer). Two colors can be separated and detected by two-color emission filters at the detection module (PMT module 178). The cartridge 100 can have single color capabilities for DNA fragment analysis applications and also can be upgraded to have two-color detecting capabilities for other applications. Reference is made to U.S. Provisional Application No. 60/348,034 entitled "A Portable Multi-color Multiplexed Analysis Electrophoretic Device," filed on Oct. 19, 2001, which is commonly assigned to BioCal Technology, Inc., the assignee of the present invention, and which is fully incorporated by reference herein.

Detection System

U.S. patent application Ser. No. 10/060,052 entitled Optical Detection in A Multi-Channel Bio-Separation System, concurrently filed on Jan. 28, 2002, which is assigned to BioCal Technology, Inc., the assignee of the present invention, and which had been fully incorporated by reference herein, is more specifically directed to the time staggered/multiplexed detection scheme that can be adopted in the CE system 200 in which the cartridge 100 is designed to be used.

Figure 16:
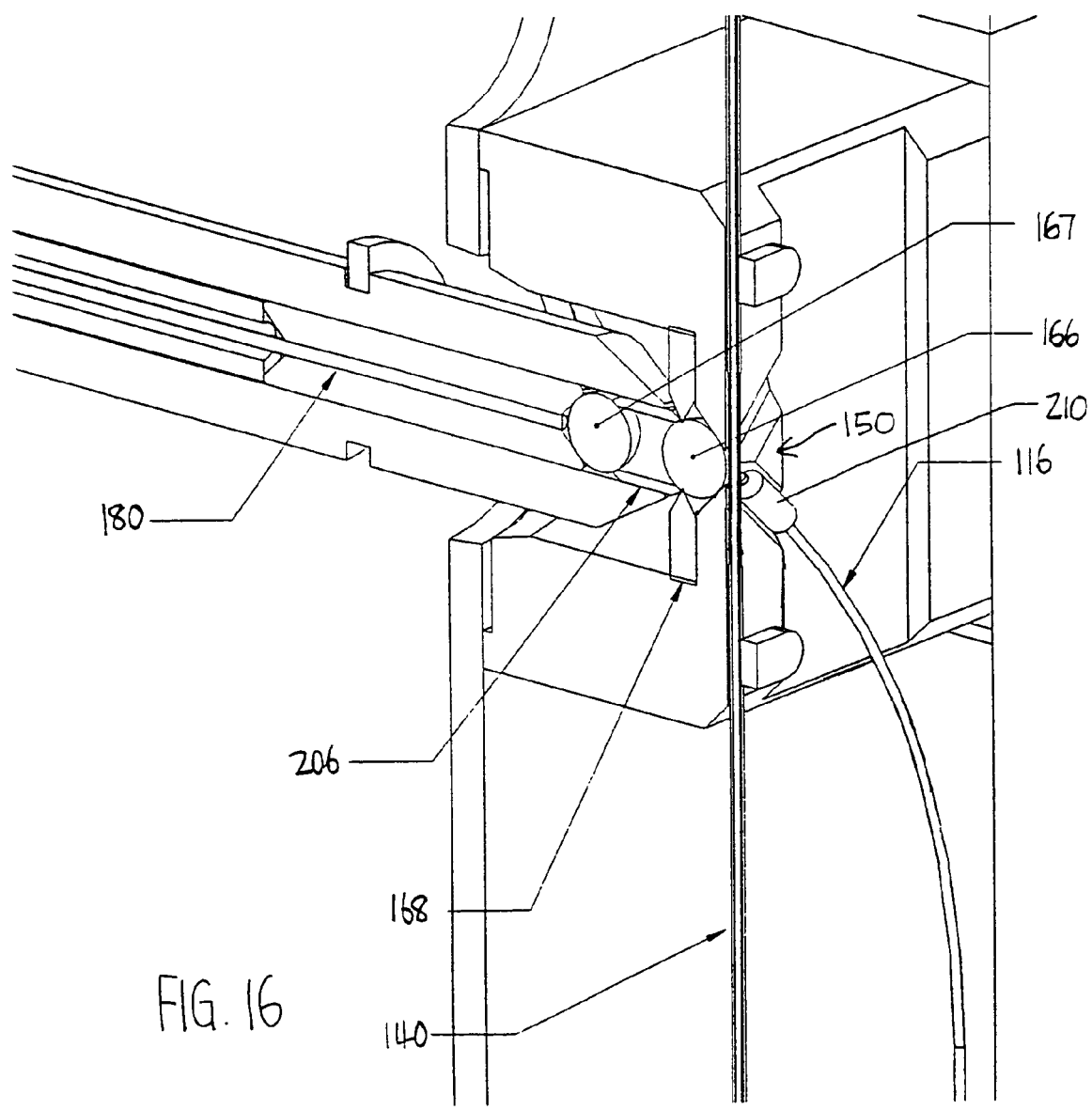
FIG. 16 is a perspective sectional view of the cartridge section B shown in FIG. 13.

A closer look at section B in FIG. 13 shows the detection, or emission, system in FIG. 16. Excitation light from a light source (e.g., LED 184) travels in the excitation fiber 116 to the detection zone 155 of the capillary 140. A fiber ferrule 210 (FIG. 16) strengthens and protects the excitation fiber 116 that is inserted within each V-groove block 150. Two excitation fibers 116 may be guided to one V-groove block 150, both directing light from the two lower angle openings 154 and 156 of the V-groove block 150. The preferred embodiment for aligning each excitation fiber with a capillary is a single block featuring machined V-grooves that nest both the capillary and the fiber in precise alignment to each other. The block may be manufactured by using tooling for a coined part or by injection molding. Also, a cross drilled screw machine part may be used in which the capillary and fibers would be loaded in precisely machined holes rather than in V-grooves.

Figure 17:
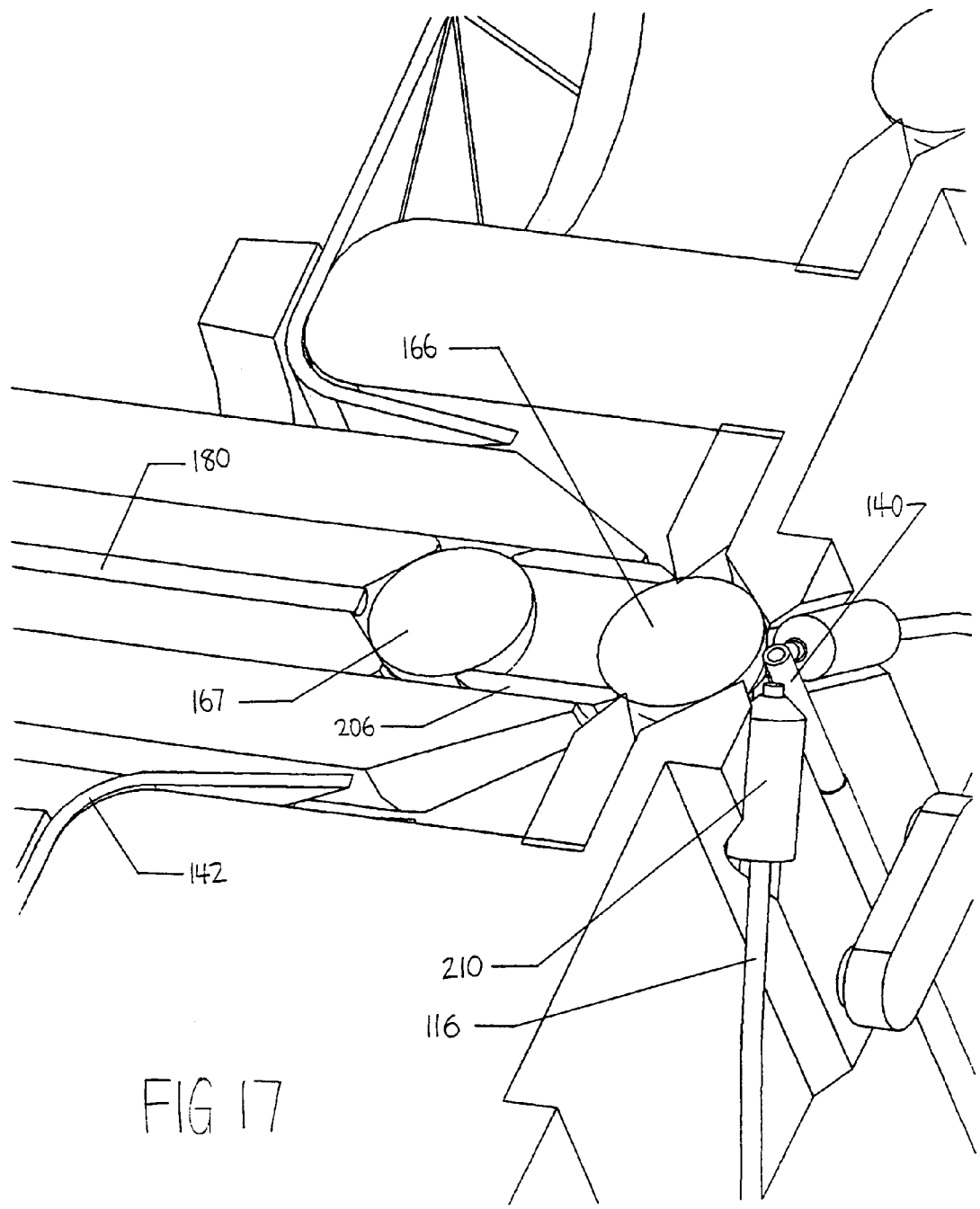
FIG. 17 is perspective sectional view of the detection zone with lens, probe, capillary, and excitation fiber.

When the excitation light is directed at the detection zone 155 (also see FIG. 17), the detection system detects emitted light, or emission signals at 90 degrees with respect to the excitation plane. Collimation optics for collimating the emission beam is needed since the emission fiber 180 is outside the liquid or gel. The Numerical Aperture of the excitation fiber 116 determines the amount of power density launched inside the gel close to the detection zone. The excitation light source may be a LED 184, which is relatively inexpensive, or a laser (may be a solid state laser, gas laser, dye laser or the like). The fluorescence emissions from the separated components or analytes at the detection zone is collected through micro-lenses 166 and 167, and directed through an emission collection fiber 180 to a detector. Between these two ball lenses 166 and 167 is a spacer 206. The capillary 140 may have transparent walls, or opaque walls provided with a transparent window to direct emissions to the micro-lenses 166 and 167. The lens 166 is used for collecting emissions and preferably has a high collection angle property (e.g., a sapphire micro-lens with index of refraction of n=1.76 from Swiss Jewel Company Model # B2.00 that has a short focal distance with a high numerical aperture (N.A.)). The lens 167 is for coupling the collimated emission light produced by the sapphire lens to the emission fiber 180 (e.g., a BK-7 micro-lens, available from the Swiss Jewel Co.). The fluorescent light, which has a higher wavelength (e.g., 570 to 630 nm) than the excitation light, is then routed by a large core optical fiber 180 (370 μm O.D., 0.22 NA fibers, but could also be in ranges of: 100-1000 μm O.D., 0.12-0.5 NA) to a detector (e.g., R5984 Hamamatsu photomultiplier tube (PMT)) after going through color separation (e.g., using 570-630 nm) long pass emission filters. The emission signals are relayed by emission fibers 180 into the detector module (PMT detector 178) where they are filtered by a single or multiple emission filter 176 and are read (detected) in a time-multiplexed (time-staggered) scheme. The detection fiber 180 can be seen more clearly in connection with the detection optics system as described and shown in FIG. 13.

It is further noted that the detection zone is not necessarily a well-defined zone with well-defined boundaries, due to the nature of the substance, the incident radiation, and the fluorescence emissions. It is generally a zone in which light from the excitation fiber is directed to cause fluorescence emissions and the detection optics is aimed to capture part of such fluorescence emissions. Light from the excitation fiber may cause fluorescence emissions outside the detection zone, and some of the emissions from within the zone may not be detected by the detection optics. The closer the excitation fiber is to the detection zone or the higher the power density of excitation light, the stronger the collected emission signals are.

In the multi-capillary CE device of the present invention, the fluorescence excitation light sources may be super bright blue or green LEDs. The attractive features of LEDs as light sources are their low cost, small size, long lifetime, good intensity and stability resulting in low noise, and the possibility of direct electronic modulation of the intensity. The LEDs contemplated in this invention are based on InGaN material technology (e.g., HLMP-CB 15 and HLMP-CM15 from Agilent) with an average light output power of 2.5-3 mW. The spectral characteristics with its peak wavelength and halfwidth (nm) of the InGaN LEDs indicate that these LEDs can be used for excitation of fluorescence with excitation spectra in the range of 440 to 570 nm (e.g., fluorescin, rhodamine, Etidium Bromide, thiazol orange) and for frequency in the range of 1 Hz to 100 MHz. Since the response time of these LEDs are very high (at a few hundred nanoseconds), they can be pulsed at greater forward currents, up to 100 mA in pulsed mode operation, to obtain high radiant peaks. Pulsed operation of LEDs can typically be achieved by the transistor drive circuits. Significantly higher peak LED light output can be realized from large drive current pulses at low duty cycles (i.e., 5%, 10%, 25% or 50%) than DC operation.

Different color LEDs (i.e., blue or green LEDs) could be used as excitation sources for excitation of different fluorophores (different applications). The preferred embodiment uses LEDs in wavelength ranges of 500-600 nm, and specifically at 524 nm. A second LED module, or a second color LED, could be added to the current design for a dual-wavelength detection device either bringing two wavelengths to the micro-channel using one or two fibers. The current detection/separation platform could be expanded with dual LED modules by having excitation and collection optics with a second PMT to provide a multi-wavelength fluorescence detection DNA fragment detector.

The excitation light sources could be changed from LEDs to Laser Diodes (semiconductor solid-state lasers). Alternatively, they could be pulsed lasers (e.g., solid state lasers, gas lasers, dye lasers, fiber lasers). The main reason for using LEDs (i.e., Green, 524 nm) is their low cost, super brightness, and small package. Surface Mount (SMT) type LEDs could also be used, using either fiber coupled or direct butt-to-butt coupled scheme to capillaries to deliver excitation light to the separating analytes. An alternate light source for this instrument would be laser diodes in the range of 400-800 nm.

A person skilled in the art will recognize that the instrument incorporating the essence of this invention can also be used for other biomoleculer analysis. For example, by altering the separation gel or buffer, the system can also be modified to analyze biomolecules like proteins, carbohydrates, and lipids. Using a number of multi-channel cartridges of the present invention having different buffer/gel chemistries, capillaries, etc., particular buffer/gel chemistry, with matching capillary (e.g., with particular internal wall coatings and column sizes), may be easily interchanged to suit the particular sample based separation applications and run conditions, to achieve different separations, types, speeds, resolutions, etc. The same cartridge may be set aside, and later reused for conducting future separation runs. Compared to the prior art CE systems, the set up time to prepare the present CE system 200 using the cartridge 100 to run different test can be reduced significantly, since the separation column, the separation medium, and at least the detection optics requiring fine alignment with respect to the capillaries are all self contained within the cartridges. The reusability of the cartridge significantly reduces the material cost for the CE system. Also since the gel matrix with intercalated dye is hermetically sealed inside cartridge it provides a good solution for an environmentally safe/ "Green" product. The fluorophore and/or gel matrix may contain carcinogens and other materials harmful to health and environment. By packaging the gel inside the cartridge, it significantly ease handling and improve safety. The cartridge may be collected and disposed of accordingly in an environmentally safe manner, or it can be recyclable, with spent parts replaced or refurbished by trained technicians to avoid harm to the environment.

With this automated and modular with integrated optics and self-aligning (non-moving micro-optical parts) multi-channel approach the operation of the instrument becomes simpler, more reliable yet provides high throughput. The cartridge 100 with self-contained, pre-aligned optics with respect to the separation channels, can be easily snapped into the CE system 200. Further, this multi-channel detection scheme could be expanded or scaled up to more than 12 or even $N^{th}$ number of detection channels (e.g. 96-channels) without impairing the detection sensitivity. The other advantage of this simple time-multiplexed type detection method is that there is negligible or no cross talk between the channels compared with any other high-throughput LIF detection schemes.

While in the embodiments described above, the multiple radiation sources are at the same wavelength, it is within the scope and spirit of the present invention to configure the multiple radiation sources at different wavelengths, to complement the specific samples, sample based detection applications or gel chemistries in the different capillaries.

Incident radiation for the detection may be directed at the detection zone and/or radiation emissions from the detection zone may be output axially along the separation medium. A widened detection zone may be adopted. References are made to U.S. patent application Ser. No. 09/887,871 entitled Optical Detection in Bio-Separation Device Using Axial Radiation Input, U.S. patent application Ser. No. 09/887,953 entitled Optical Detection in Bio-Separation Device Using Axial Radiation Output, and U.S. patent application Ser. No. 09/887,872, now U.S. Pat. No. 6,529,275, entitled Optical Detection in Bio-Separation Device Using a Widened Detection Zone, all filed on Jun. 22, 2001, which are commonly assigned to BioCal Technology, Inc., the assignee of the present invention, and which are fully incorporated by reference herein.

The low cost instrument of the present invention has a disposable/recyclable multi-channel cartridge design (since, most of the cartridge body parts could be retrieved and then repackaged or reused. The only part that would be replaced are the capillaries and the gel), a fluorescence detection system, and a built-in sample handling tray (96-well plate) mechanism. Experiments have demonstrated the analyses of samples are completed in just 4 to 10 minutes per twelve-channel (twelve parallel results for twelve test samples). The DNA analyzing system is an all-in-one high throughput workstation that handles complete DNA fragment analysis from injection to detection to fragment data collection. Detection sensitivity for a single capillary using the described detection mode of the present invention is in the order of 0.02 ng of the DNA fragment in less than 10 minutes of separations (using HaeIII digest φX174 bacteriophage DNA test mix). This kind of approach for having twelve micro-channels/capillaries running in parallel produces results within 10 minutes for all twelve electrophoresed samples. This kind of separation speed and detection sensitivity is several orders of magnitude better than conventional slab gel-electrophoresis techniques.

While the invention has been particularly shown and described with reference to the preferred embodiments, it will be understood by those skilled in the art that various changes in form and detail may be made without departing from the spirit, scope, and teaching of the invention. For example, the excitation radiation source could be, for example, LEDs, Laser Diodes (semiconductor solid-state lasers), pulsed lasers (e.g., solid state lasers, gas lasers, dye lasers, fiber lasers), or other sources of radiation. LEDs (e.g., Green, 524 nm) are associated with low cost, super brightness, and small package. Alternate relative inexpensive light source for the present invention could be laser diodes in the visible, UV and/or infrared range. For example, laser diodes in the range of 400-900 nm, and more specifically in the range of 400-600 nm may be used, for example.

A person skilled in the art will recognize that the instrument incorporating the essence of this invention can also be used for biomoleculer analysis other than DNA analysis. For example, by altering the separation gel or buffer, the system can also be modified to analyze biomolecules like proteins, carbohydrates, and lipids.

By way of example and not limitation, the detection scheme of the present invention is described in connection with capillary electrophoresis and radiation induced fluorescence detection. It is understood that the present invention is also applicable to detection of analytes separated based on bio-separation phenomenon other than electrophoresis, and detection of radiation emissions other than fluorescence emissions, including other types of emissive radiation, such as phosphorescence, luminescence and chemiluminescence, as well as absorbance based detection.

Furthermore, while the separation channels in the described embodiments are defined by cylindrical columns or tubes, it is understood that the concepts of the present invention is equally applicable to separation channels defined by open channels, for example micro-channels defined by etching in a substrate (micro-fluidics type devices or bio-chips).

The transport mechanism can be configured to move the trays in a horizontal plane, and an additional transport mechanism may be provided to move the cartridge vertically to access the trays.

Accordingly, the disclosed invention is to be considered merely as illustrative and limited in scope only as specified in the appended claims.

We claim:

1. A multi-channel cartridge for bio-separation, comprising:
   a body;
   a plurality of capillary separation channels for analytes, the capillary separation channels are defined and isolated from one another by physical walls in the body, wherein the analytes are confined to migrate within boundary of the physical walls;
   a chamber in the body defining a reservoir in fluid flow communication common with the capillary separation channels, said chamber containing a separation support medium which is sealed from leakage when the cartridge is handled in any orientation; and
   built-in optics integrally supported within the body, the built-in optics being aligned with respect to a section of each capillary separation channel to define a detection zone for at least one of incident radiation and radiation output.

2. The multi-channel cartridge as in claim 1, characterized by at least one of the following: portable, recyclable, reusable and interchangeable with other cartridges having different one of separation support medium and capillary separation channels.

3. The multi-channel cartridge as in claim 1, further comprising an electrode electrically coupled to the reservoir.

4. The multi-channel cartridge as in claim 3, wherein each capillary separation channel comprises a further electrode electrically coupled to an end thereof, said end being an end that is away from the reservoir.

5. The multi-channel cartridge as in claim 1, wherein the optics comprises optic fibers having an end aligned by the body to the capillary separation channels.

6. The multi-channel cartridge as in claim 5, wherein the optics further comprises optic fibers having another end positioned by the body for coupling to external radiation sources.

7. The multi-channel cartridge as in claim 1, wherein the body comprises separately replaceable capillary columns defining the physical walls of the capillary separation channels.

8. The multi-channel cartridge as in claim 1, wherein the separation support medium comprises a gel.

9. The multi-channel cartridge as in claim 8, wherein the gel is of a type suitable for capillary electrophoresis.

10. The multi-channel cartridge as in claim 8, wherein the gel comprises a composition that permits spent gel in the capillary separation channels to be replaced by fresh gel in the reservoir.

11. The multi-channel cartridge as in claim 1, further comprising an interface for introducing pressurized air into the reservoir to purge and fill the capillary separation channels with the separation support medium.

12. The multi-channel cartridge as in claim 1, wherein each capillary separation channel has a first end in fluid flow communication with the reservoir and a second end that extends away from the reservoir, and wherein the detection zone is defined closer to the first end than the second end.

13. The multi-channel cartridge as in claim 12, wherein the second end of the capillary channel is open to allow input of a sample through the second end.

14. A bio-separation system, comprising:
   a base;
   a multi-channel cartridge for bio-separation supported on the base, comprising:
      a body;
      a plurality of separation channels, the capillary separation channels are defined and isolated from one another by physical walls in the body, each separation channel defining a detection zone, wherein analytes are confined to migrate within boundary of the physical walls;
      a chamber in the body defining a reservoir in fluid flow communication common with the separation channels, said chamber containing a separation support medium which is sealed from leakage when the cartridge is handled in any orientation;
      built-in optics integrally supported within the body, the built-in optics being aligned with respect to a section of each capillary separation channel to define a detection zone for at least one of incident radiation and radiation output;
   a positioning mechanism positioning a container of samples supported in a horizontal plane with respect to the multi-channel cartridge such that the separation uliariueb arc in fluid communication with the container;
   a separation mechanism effecting bio-separation of the samples along the separation channels; and
   a controller controlling operations of the positioning mechanism and separation mechanism.

15. The bio-separation system as in claim 14, further comprising:
   a radiation source directing radiation at the detection zone; and
   a detector detecting radiation from the detection zone.

16. The bio-separation system as in claim 14, wherein the separation mechanism comprises an electrophoretic mechanism effecting electrophoresis separation of the samples in the separation channels.

17. The bio-separation system as in claim 14, further comprising pressure mechanism pressurizing the reservoir to purge and fill the separation channels.

18. The bio-separation system as in claim 14, wherein the body comprises discrete capillary columns defining the physical walls of the separation channels.

19. A bio-separation system, comprising:
a container supporting samples in a horizontal plane;
a multi-channel cartridge for bio-separation, comprising:
  a body;
  a plurality of separation channels, the capillary separation channels are defined and isolated from one another by physical walls in the body, each separation channel having a detection tone, wherein analytes are confined to migrate within boundary of the physical wails;
  a chamber in the body defining a reservoir in fluid flow communicating common with the separation channels, said chamber containing a separation support medium which is sealed from leakage when the cartridge is handled in any orientation; and
  a positioning mechanism, positioning the container of samples with respect to the multi-channel cartridge such that the separation channels are in fluid communication with the container; and
  wherein the multi-channel cartridge further comprises built-in optics integrally supported within the body, which is aligned with respect to the detection zone for at least one of incident radiation and radiation output, and an electrode electrically coupled to the reservoir,
a controller controlling operations of the positioning mechanism.

20. The bio-separation system as in claim 19, further comprising:
a radiation source directing radiation at the detection zone; and
a detector detecting radiation from the detection zone.

21. The bio-separation system as in claim 19, further comprising a separation mechanism that comprises a voltage source providing an electrical potential to effect electrophoresis separation of the samples in the separation channels.

22. The bio-separation system as in claim 19, further comprising a pressure mechanism pressurizing the reservoir to purge and fill the separation channels.

* * * * *